US009832510B2

(12) United States Patent
Tegreene et al.

(10) Patent No.: US 9,832,510 B2
(45) Date of Patent: Nov. 28, 2017

(54) DECEPTIVE INDICIA PROFILE GENERATION FROM COMMUNICATIONS INTERACTIONS

(75) Inventors: Clarence T. Tegreene, Mercer Island, WA (US); Royce A. Levien, Lexington, MA (US); Richard T. Lord, Tacoma, WA (US); Robert W. Lord, Seattle, WA (US); Mark A. Malamud, Seattle, WA (US)

(73) Assignee: Elwha, LLC, Bellevue, WA (US)

( * ) Notice: Subject to any disclaimer, the term of this patent is extended or adjusted under 35 U.S.C. 154(b) by 934 days.

(21) Appl. No.: 13/385,781

(22) Filed: Mar. 6, 2012

(65) Prior Publication Data

US 2013/0139257 A1 May 30, 2013

Related U.S. Application Data

(63) Continuation-in-part of application No. 13/373,799, filed on Nov. 30, 2011, and a continuation-in-part of
(Continued)

(51) Int. Cl.
*G06F 21/00* (2013.01)
*H04N 21/422* (2011.01)
(Continued)

(52) U.S. Cl.
CPC ......... *H04N 21/42201* (2013.01); *A61B 5/16* (2013.01); *H04N 21/4394* (2013.01);
(Continued)

(58) Field of Classification Search
CPC .............................................. H04N 21/42201
(Continued)

(56) References Cited

U.S. PATENT DOCUMENTS 4,008,714 A 2/1977 Silva et al.
5,771,261 A 6/1998 Anbar
(Continued)

FOREIGN PATENT DOCUMENTS

EP 1872719 A1 2/2008

OTHER PUBLICATIONS

"Continuous Noninvasive Blood Pressure Measurement by Near Infra Red CCD Camera and Pulse Transmit Time System"—Zurek, P. Krejcar, O. Penhaker, M. Cerny, M. Frischer, R., 2010 Second International Conference on Computer Engineering and Applications (ICCEA); Issue Date: Mar. 19-21, 2010; vol. 2, pp. 449-453.
(Continued)

*Primary Examiner* — Morshed Mehedi

(57) ABSTRACT

Systems, methods, computer-readable storage mediums including computer-readable instructions and/or circuitry for generating deceptive indicia profiles may implement operations including, but not limited to: detecting one or more indicia of deception associated with one or more signals associated with communication content provided by a participant in a first communications interaction; detecting one or more indicia of deception associated with one or more signals associated with communications content provided by the participant in a second communications interaction; generating a deceptive indicia profile for the participant according to indicia of deception detected in the communications content provided by the participant in the first communications interaction and indicia of deception detected in the communications content provided by the participant in the second communications interaction; and providing a notification associated with the deceptive indicia profile for the participant to the participant.

24 Claims, 13 Drawing Sheets

Related U.S. Application Data application No. 13/373,798, filed on Nov. 30, 2011, and a continuation-in-part of application No. 13/373,938, filed on Dec. 5, 2011, and a continuation-in-part of application No. 13/374,516, filed on Dec. 30, 2011, and a continuation-in-part of application No. 13/374,521, filed on Dec. 30, 2011.

(51) Int. Cl.

| | | |
|---|---|---|
| H04N 21/439 | (2011.01) | |
| H04N 21/44 | (2011.01) | |
| H04N 21/442 | (2011.01) | |
| H04N 21/4788 | (2011.01) | |
| H04N 21/84 | (2011.01) | |
| A61B 5/16 | (2006.01) | |
| A61B 5/021 | (2006.01) | |
| A61B 5/024 | (2006.01) | |

(52) U.S. Cl.
CPC .. *H04N 21/44008* (2013.01); *H04N 21/44218* (2013.01); *H04N 21/4788* (2013.01); *H04N 21/84* (2013.01); *A61B 5/021* (2013.01); *A61B 5/024* (2013.01)

(58) Field of Classification Search
USPC ....................................................... 726/22–23
See application file for complete search history.

(56) References Cited

U.S. PATENT DOCUMENTS

| | | | |
|---|---|---|---|
| 5,853,005 A * | 12/1998 | Scanlon | 600/459 |
| 6,837,615 B2 | 1/2005 | Newman | |
| 6,959,322 B2 | 10/2005 | Ludwig et al. | |
| 6,996,256 B2 | 2/2006 | Pavlidis | |
| 7,027,621 B1 | 4/2006 | Prokoski | |
| 7,111,980 B2 | 9/2006 | Pavlidis et al. | |
| 7,138,905 B2 | 11/2006 | Pavlidis et al. | |
| 7,321,855 B2 | 1/2008 | Humble | |
| 7,388,971 B2 * | 6/2008 | Rice et al. | 382/118 |
| 7,437,766 B2 | 10/2008 | Cohen et al. | |
| 7,849,502 B1 | 12/2010 | Bloch et al. | |
| 7,853,445 B2 * | 12/2010 | Bachenko et al. | 704/9 |
| 7,899,524 B2 | 3/2011 | Kozel | |
| 8,145,474 B1 | 3/2012 | Daily et al. | |
| 8,145,562 B2 * | 3/2012 | Wasserblat et al. | 705/38 |
| 8,224,907 B2 | 7/2012 | Cohen et al. | |
| 8,347,399 B2 | 1/2013 | Levien et al. | |
| 8,543,196 B2 | 9/2013 | Ning | |
| 8,577,446 B2 | 11/2013 | Kyle et al. | |
| 2002/0066034 A1 | 5/2002 | Schlossberg et al. | |
| 2002/0078357 A1 | 6/2002 | Bruekers et al. | |
| 2003/0012253 A1 | 1/2003 | Pavlidis | |
| 2003/0149344 A1 | 8/2003 | Nizan | |
| 2003/0236995 A1 | 12/2003 | Fretwell, Jr. | |
| 2004/0143170 A1 | 7/2004 | DuRousseau | |
| 2004/0181145 A1 | 9/2004 | Al Bandar et al. | |
| 2005/0097320 A1 * | 5/2005 | Golan et al. | 713/166 |
| 2005/0143629 A1 * | 6/2005 | Farwell | 600/300 |
| 2005/0144256 A1 | 6/2005 | Blumberg | |
| 2005/0185779 A1 * | 8/2005 | Toms | 379/114.14 |
| 2005/0232471 A1 | 10/2005 | Baer | |
| 2005/0240956 A1 | 10/2005 | Smith et al. | |
| 2005/0288954 A1 * | 12/2005 | McCarthy et al. | 705/1 |
| 2006/0123482 A1 * | 6/2006 | Aaron | 726/25 |
| 2007/0010993 A1 | 1/2007 | Bachenko et al. | |
| 2007/0038778 A1 | 2/2007 | Miao et al. | |
| 2007/0177017 A1 | 8/2007 | Kyle et al. | |
| 2007/0192108 A1 | 8/2007 | Konchitsky | |
| 2007/0213981 A1 | 9/2007 | Meyerhoff et al. | |
| 2007/0214504 A1 * | 9/2007 | Milani Comparetti et al. | 726/23 |
| 2007/0270659 A1 | 11/2007 | Giegerich | |
| 2007/0294122 A1 | 12/2007 | Johnston | |
| 2008/0059198 A1 | 3/2008 | Maislos et al. | |
| 2008/0208016 A1 * | 8/2008 | Hughes et al. | 600/301 |
| 2008/0260212 A1 | 10/2008 | Moskal et al. | |
| 2008/0282324 A1 | 11/2008 | Hoal | |
| 2009/0023422 A1 | 1/2009 | MacInnis et al. | |
| 2009/0023428 A1 | 1/2009 | Behzad et al. | |
| 2009/0177979 A1 * | 7/2009 | Garbow et al. | 715/757 |
| 2009/0193293 A1 | 7/2009 | Stolfo et al. | |
| 2009/0254988 A1 * | 10/2009 | Nonaka et al. | 726/22 |
| 2009/0254998 A1 * | 10/2009 | Wilson | 726/27 |
| 2009/0299154 A1 | 12/2009 | Segman | |
| 2010/0039218 A1 | 2/2010 | Cohen et al. | |
| 2010/0042667 A1 | 2/2010 | Cohen et al. | |
| 2010/0042669 A1 | 2/2010 | Cohen et al. | |
| 2010/0067798 A1 | 3/2010 | Hung et al. | |
| 2010/0085414 A1 | 4/2010 | Eun et al. | |
| 2010/0099975 A1 | 4/2010 | Faro et al. | |
| 2010/0132038 A1 * | 5/2010 | Zaitsev | 726/22 |
| 2010/0191077 A1 | 7/2010 | O'Kane | |
| 2010/0246835 A1 | 9/2010 | Dooling et al. | |
| 2010/0318595 A1 | 12/2010 | Cohen et al. | |
| 2011/0004939 A1 | 1/2011 | Cohen et al. | |
| 2011/0004940 A1 | 1/2011 | Cohen et al. | |
| 2011/0035472 A1 | 2/2011 | Tucker et al. | |
| 2011/0041061 A1 | 2/2011 | Cohen et al. | |
| 2011/0041185 A1 | 2/2011 | Cohen et al. | |
| 2011/0043759 A1 | 2/2011 | Bushinsky | |
| 2011/0081018 A1 | 4/2011 | Cohen et al. | |
| 2011/0083010 A1 | 4/2011 | Cohen et al. | |
| 2011/0093806 A1 | 4/2011 | Cohen et al. | |
| 2011/0107427 A1 | 5/2011 | Cohen et al. | |
| 2011/0110518 A1 | 5/2011 | Cohen et al. | |
| 2011/0131409 A1 | 6/2011 | Cohen et al. | |
| 2011/0154020 A1 | 6/2011 | Cohen et al. | |
| 2011/0161217 A1 | 6/2011 | Cohen et al. | |
| 2011/0166972 A1 | 7/2011 | Cohen et al. | |
| 2011/0166973 A1 | 7/2011 | Cohen et al. | |
| 2011/0166974 A1 | 7/2011 | Cohen et al. | |
| 2011/0169603 A1 | 7/2011 | Fithian et al. | |
| 2011/0173440 A1 | 7/2011 | Cohen et al. | |
| 2011/0176667 A1 * | 7/2011 | Kumar | 379/142.04 |
| 2011/0181684 A1 | 7/2011 | Salamatov et al. | |
| 2011/0224979 A1 | 9/2011 | Raux | |
| 2011/0295392 A1 | 12/2011 | Cunnington et al. | |
| 2012/0150762 A1 | 6/2012 | Ormerod | |
| 2012/0254333 A1 * | 10/2012 | Chandramouli et al. | 709/206 |
| 2013/0046531 A1 | 2/2013 | Chandramouli et al. | |
| 2013/0138428 A1 | 5/2013 | Chandramouli et al. | |
| 2013/0145465 A1 | 6/2013 | Wang et al. | |
| 2014/0013426 A1 | 1/2014 | Douceur et al. | |
| 2014/0234815 A1 | 8/2014 | Jang et al. | |
| 2014/0278629 A1 | 9/2014 | Stephenson et al. | |
| 2014/0355861 A1 | 12/2014 | Nirenberg et al. | |
| 2015/0050930 A1 | 2/2015 | Seo et al. | |
| 2015/0095162 A1 | 4/2015 | Jakobson et al. | |
| 2015/0304492 A1 | 10/2015 | Eyeson | |

OTHER PUBLICATIONS

"A novel method to detect Heart Beat Rate using a mobile phone"—2010 Annual International Conference of the IEEE Engineering in Medicine and Biology Society (EMBC); Pelegris, Banitsas, Orbach and Marias; Aug. 31, 2010-Sep. 4, 2010; pp. 5488-5491.

"Towards Macro- and Micro-Expression Spotting in Video Using Strain Patterns"—Shreve, Godavarthy, Manohar, Goldgof, Sarkar; Dec. 7-8, 2009; pp. 1-6; http://figment.csee.usf.edu/~vmanohar/WACV09_Expression_Spotting.pdf; Printed Feb. 28, 2012.

* cited by examiner

400

402 detecting one or more indicia of deception associated with one or more signals associated with communication content provided by a participant in a first communications interaction

| 602 detecting a heart rate of the first participant providing the communication content | 604 detecting a blood pressure of the first participant providing the communication content | 606 detecting a perspiration level of the first participant providing the communication content | 608 detecting a breathing rate of the first participant providing the communication content |
|---|---|---|---|

404 detecting one or more indicia of deception associated with the one or more signals associated with communications content provided by the participant in a second communications interaction

| 602 detecting a heart rate of the first participant providing the communication content | 604 detecting a blood pressure of the first participant providing the communication content | 606 detecting a perspiration level of the first participant providing the communication content | 608 detecting a breathing rate of the first participant providing the communication content |
|---|---|---|---|

406 generating a deceptive indicia profile for the participant according to indicia of deception detected in the communications content provided by the participant in the first communications interaction and indicia of deception detected in the communications content provided by the participant in the second communications interaction

408 providing a notification associated with the deceptive indicia profile for the participant to the participant

FIG. 6

DECEPTIVE INDICIA PROFILE GENERATION FROM COMMUNICATIONS INTERACTIONS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of the United States patent application filed under U.S. patent application Ser. No. 13/373,799, entitled DECEPTIVE INDICIA NOTIFICATION IN A COMMUNICATION INTERACTION, naming Clarence T. Tegreene, as inventor, filed Nov. 30, 2011, which is currently co-pending or is an application of which a currently co-pending application is entitled to the benefit of the filing date.

For purposes of the USPTO extra-statutory requirements, the present application constitutes a continuation-in-part of the United States patent application filed under U.S. patent application Ser. No. 13/373,798, DECEPTIVE INDICIA NOTIFICATION IN A COMMUNICATION INTERACTION, naming Clarence T. Tegreene, as inventor, filed Nov. 30, 2011, which is currently co-pending or is an application of which a currently co-pending application is entitled to the benefit of the filing date.

For purposes of the USPTO extra-statutory requirements, the present application constitutes a continuation-in-part of the United States patent application filed under U.S. patent Ser. No. 13/373,938, entitled MASKING OF DECEPTIVE INDICIA IN A COMMUNICATIONS INTERACTION, naming Clarence T. Tegreene, as inventor, filed Dec. 5, 2011, which is currently co-pending or is an application of which a currently co-pending application is entitled to the benefit of the filing date.

For purposes of the USPTO extra-statutory requirements, the present application constitutes a continuation-in-part of the United States patent application filed under U.S. patent application Ser. No. 13/374,516, entitled DETECTION OF DECEPTIVE INDICIA MASKING IN A COMMUNICATIONS INTERACTION, naming Clarence T. Tegreene, as inventor, filed Dec. 30, 2011, which is currently co-pending or is an application of which a currently co-pending application is entitled to the benefit of the filing date.

For purposes of the USPTO extra-statutory requirements, the present application constitutes a continuation-in-part of the United States patent application filed under U.S. patent application Ser. No. 13/374,521, entitled DECEPTIVE INDICIA PROFILE GENERATION FROM COMMUNICATIONS INTERACTIONS, naming Clarence T. Tegreene, as inventor, filed Dec. 30, 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Systems, methods, computer-readable storage mediums including computer-readable instructions and/or circuitry for masking deceptive indicia in communications content may implement operations including, but not limited to: detecting one or more indicia of deception associated with one or more signals associated with communication content provided by a participant in a first communications interaction; detecting one or more indicia of deception associated with one or more signals associated with communications content provided by the participant in a second communications interaction; generating a deceptive indicia profile for the participant according to indicia of deception detected in the communications content provided by the participant in the first communications interaction and indicia of deception detected in the communications content provided by the participant in the second communications interaction; and providing a notification associated with the deceptive indicia profile for the participant to the participant.

In one or more various aspects, related systems include but are not limited to circuitry and/or programming for effecting the herein referenced aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 shows an alternative embodiment of the operational procedure of FIG. 4.

DETAILED DESCRIPTION

Figure 1:
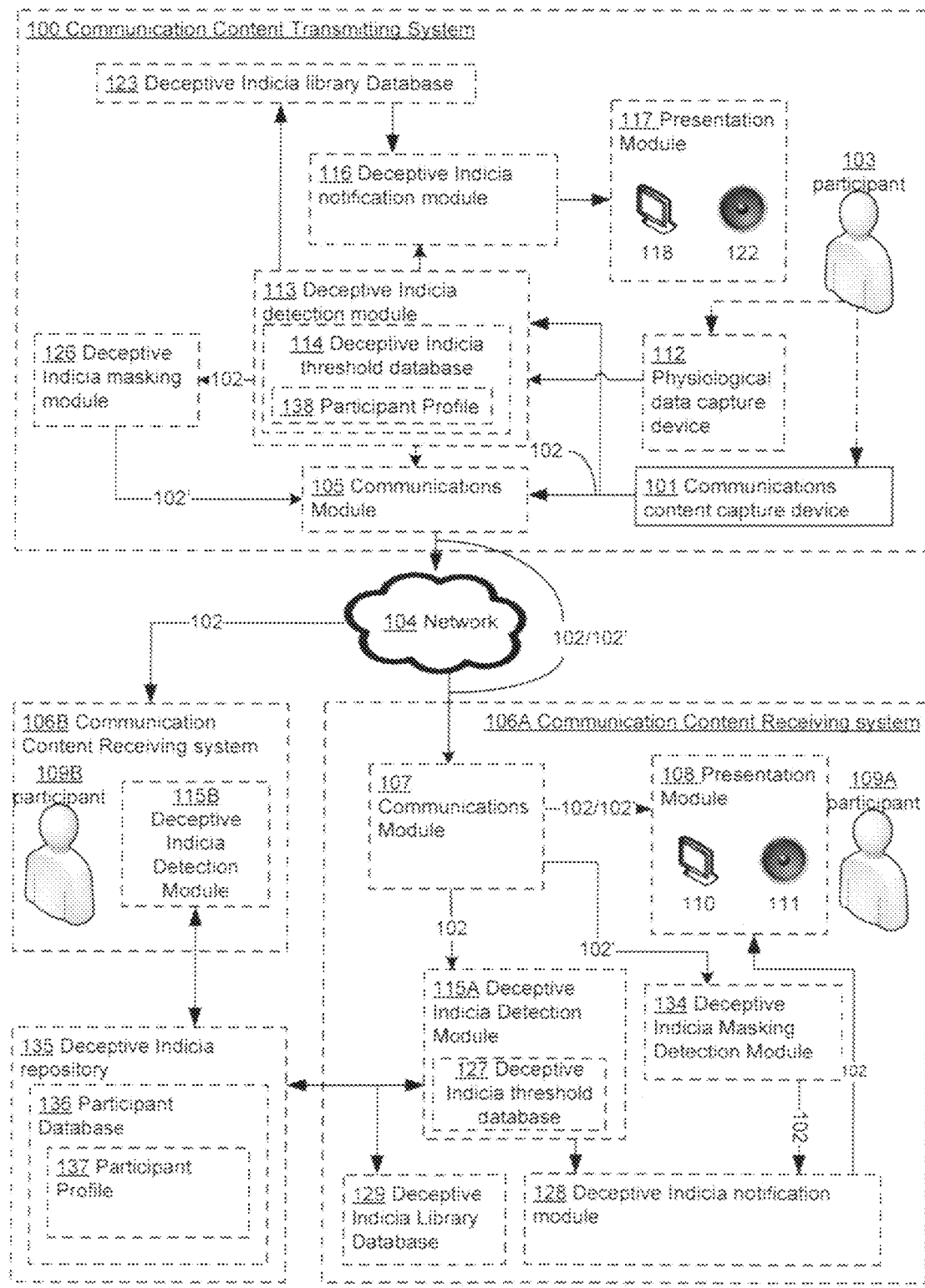
FIG. 1 shows a high-level block diagram of an operational environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Remote communication systems are ubiquitous in today's society. Individuals who are remote from one another may communicate using a plethora of communications systems such as land line telephones, mobile communication devices (e.g. mobile phones, tablet computers, etc.), networked video conferencing (e.g. Cisco TelePresence), and the like. During such communications interactions, participants may transmit and receive communications content (e.g. voice/audio data, video data, etc.) to various other remote participants.

For example, as shown in FIG. 1, a communications content transmitting system 100 may include a communications content capture device 101. The communications content capture device 101 may include, but is not limited to, a video capture device (e.g. a digital camera, web cam, teleconferencing camera, etc.), an audio capture device (e.g. a microphone, telephone), and the like. The communications content 102 captured from a content-generating participant 103 by the communications content capture device 101 may be transmitted to a communications network 104 via a communications module 105 of the communications content transmitting system 100. The communications module 105 may include a network adapter configured to translate the communications content 102 captured by the communications content capture device 101 according to a defined network protocol for the network 104 so as to enable transmission of the communications content 102 over the network 104. For example, the communications module 105 may include a wired network adapter (e.g. an Ethernet adapter), a cellular network adapter, a Wi-Fi network adapter, and the like.

As further shown in FIG. 1, the communications content 102 may be transmitted across the network 104 to a communications content receiving system 106. The communications content receiving system 106 may include a communications module 107 similar to the communications module 105 of the communications content transmitting system 100. For example, the communications module 107 may include a wired network adapter (e.g. an Ethernet adapter), a cellular network adapter, a Wi-Fi network adapter, and the like. The communications module 107 may translate communications content 102 transmitted across the network 104 according to the network protocol back into its native audio and/or video format. The communications content 102 may then be provided to a presentation module 108 where the communications content 102 may be displayed to a content-receiving participant 109 via a display device 110 in the case of video communications content 102 or broadcast to the content-receiving participant 109 via an audio speaker 111 in the case of audio communications content 102 so as to enable the content-receiving participant 109 to view and/or hear the communications content 102 generated by the content-generating participant 103.

It may be the case that such communications content 102 may be provided in the context of communications between the content-generating participant 103 and the content-receiving participant 109 where the content-generating participant 103 may have a motivation to provide deceptive information to the content-receiving participant 109. For example, the content-generating participant 103 and the content-receiving participant 109 may be communicating regarding a mutual business transaction where a negotiation of terms is occurring. As such, it may be the case that the content-generating participant 103 may attempt to present deceptive information (e.g. information which, according to one or more objective standards, is untrue) in an attempt to obtains terms of the business transaction that are more favorable for the side of the content-generating participant 103. As a specific example, the content-generating participant 103 may provide communications content 102 indicating that a maximum purchase price for a transaction is actually less that an authorized purchase price.

In such scenarios where the content-generating participant 103 may have a motivation to provide deceptive communications content 102 or, conversely, where the content-receiving participant 109 may believe that the content-generating participant 103 has such a motivation, various physiological indicia may be monitored to determine the likelihood that such deception is, in fact occurring.

For example, as shown in FIG. 1, the communications content transmitting system 100 may include a physiological data capture device 112. The physiological data capture device 112 may be a device configured to capture data associated with one or more physical conditions of the content-generating participant 103 such as heart rate, blood pressure, breathing patterns, perspiration levels, and the like. The physiological data capture device 112 may include, but is not limited to, a heart rate monitor (e.g. an EKG), a pressure transducer (e.g. a blood pressure monitoring cuff), a thermometer, a skin conductivity sensor, an IR sensor, a high-resolution camera, a microphone, and the like. Physiological data obtained by the physiological data capture device 112 may be provided to a which may analyze the physiological data (e.g. compare the data to one or more threshold levels) to determine if the physiological data represents and indicia of deception.

Additionally, the communications content 102, itself, received via the communications content capture device 101 may be provided to the deceptive indicia detection module 113 for analysis of the communications content 102 to determine if the communications content 102 represents and indicia of deception. For example, the audio and/or video of the communications content 102 may be analyzed to determine the various physiological characteristics such as heart rate, blood pressure, breathing patterns, perspiration levels as well as other parameters such as eye dilation, eye movements, voice stress, language constructs, and the like.

Upon receipt of either physiological data from a physiological data capture device 112 or the communications content 102 received from the communications content capture device 101, such data may be analyzed for correspondence with one or more defined deceptive indicia threshold values maintained in a deceptive indicia threshold database 114. Exceeding one or more deceptive indicia threshold values may be an indicator that the content-generating participant 103 is presenting one or more physiological indicators, speech patterns and/or physical movements that may be interpreted by a content-receiving participant 109 as being associated with deception in the communications content 102.

In an exemplary embodiment, the physiological data capture device 112 may include a near infra red charge-coupled device camera. The near IR CCD camera may image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate. The computed heart rate may be compared to a deceptive indicia threshold value maintained in the deceptive indicia threshold database 114. As an elevated heart rate may be an indicator of stress associated with providing deceptive communications content 102, a computed heart rate in excess of the deceptive indicia threshold value may be detected as indicia of deception in the communications content 102.

In another exemplary embodiment, the physiological data capture device 112 may include a near infra red charge-coupled device camera. The near IR CCD camera may image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

In another exemplary embodiment, the communications content capture device 101 and/or the physiological data capture device 112 may include a high-resolution camera. The high-resolution camera may image the skin surface of the content-generating participant 103. The deceptive indicia detection module 113 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the communications content capture device 101 and/or the physiological data capture device 112 may include a high-resolution camera. The high-resolution camera may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

In another exemplary embodiment, the communications content capture device 101 and/or the physiological data capture device 112 may include a microphone. The microphone may capture an audio signal (e.g. speech content, a voice print, breathing, ambient noise, etc.) of the content-generating participant 103. The deceptive indicia detection module 113 may then analyze the audio signal and detect one or more characteristics of the audio signal.

For example, the deceptive indicia detection module 113 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 113 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

In a further example, the deceptive indicia detection module 113 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 113 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

In a case where a content-generating participant 103 is presenting one or more indicia of deception (e.g. physiological indicators, speech patterns and/or physical movements) that may be interpreted/detected by a content-receiving participant 109 (e.g. detected by deceptive indicia detection module 115 associated with the communications content receiving system 106) as being associated with deception, it may be desirable for the content-generating participant 103 be made aware of such indicia of deception so that the content-generating participant 103 may take remedial steps to mitigate such indicia in a case where the content-generating participant 103 desires to avoid presenting an indication of deception in the communications content 102, or alternately, introduce indicia of deception into communications content 102 where the content-generating participant 103 desires to present a false indication of deception in the communications content 102.

As such, the communications content transmitting system 100 may include a deceptive indicia notification module 116. The deceptive indicia notification module 116 may receive one or more signals from the deceptive indicia detection module 113 indicating the presence or absence of deceptive indicia in communications content 102 being provided to the content-receiving participant 109. Upon the receipt of one or more signals associated with the presence of indicia of deception in communications content 102 from the deceptive indicia detection module 113, the deceptive indicia notification module 116 may, in turn provide one or more signals to a presentation module 117 so that an indicator associated with the indicia of deception is presented to the content-generating participant 103.

Figure 2A:
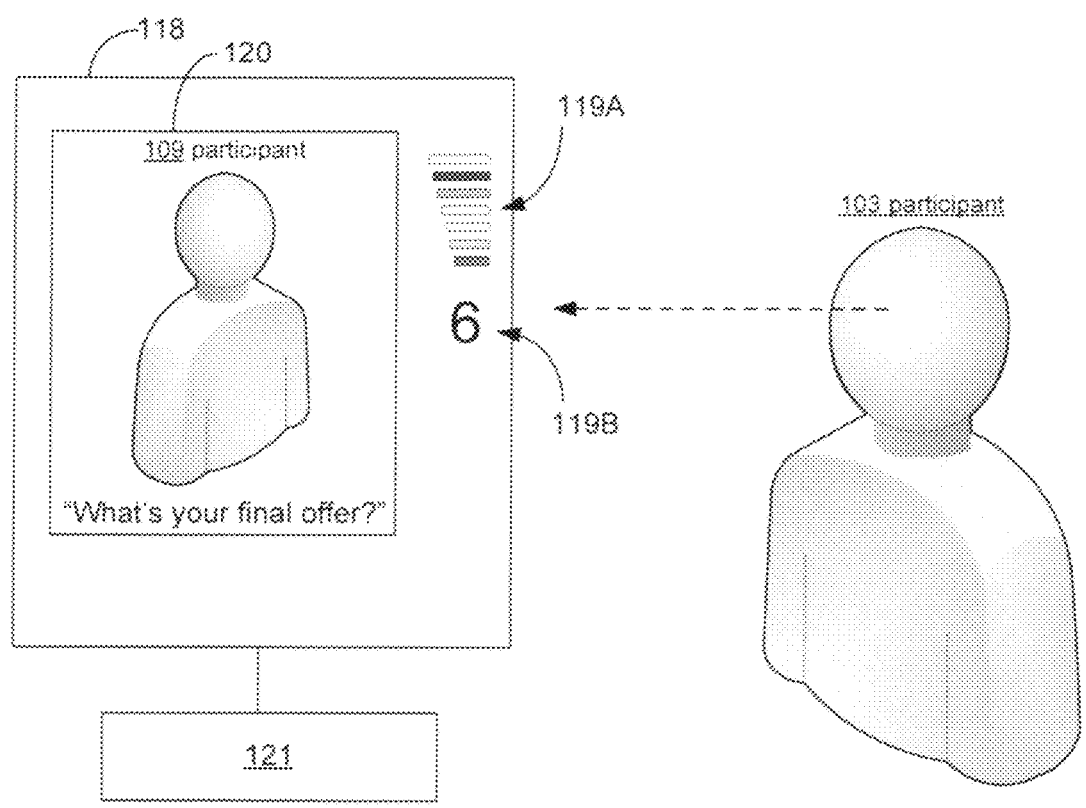
FIG. 2A shows an exemplary high-level block diagram of an exemplary system.

For example, upon the receipt of one or more signals associated with the presence of indicia of deception in communications content 102 from the deceptive indicia detection module 113, the deceptive indicia notification module 116 may provide one or more video signals to a deceptive indicia display device 118 (e.g. an LCD display) so that a visual indicator 119 associated with the indicia of deception is presented within a field of view of the content-generating participant 103. As shown in FIG. 2A, the deceptive indicia display device 118 may display a video conferencing interface 120 configured to present audio/video content from the content-receiving participant 109 during a communication interaction (e.g. at least one of audio and visual communication between at least the content-generating participant 103 and content-receiving participant 109). The deceptive indicia display device 118 may display a visual indicator 119A that presents a rate of occurrences of indicia of deception in the communications content 102, a visual indicator 119B that presents a cumulative number of occurrences of indicia of deception in the communications content 102, a color coded visual indicator 119A (e.g. "green" level indicating a low rate of occurrences of indicia of deception, a "yellow" level indicating a moderate rate of occurrences of indicia of deception, to a "red" level indicating a high rate of occurrences of indicia of deception). The visual indicator 119 may be a dynamic indicator that changes (e.g. moves from an indicated "high" rate of indicia of deception to an indicated "low" rate of indicia of deception) in real-time according to the type and/or amount of indicia of deception detected within communications content 102. The visual indicator 119 may provide an indication of the level of indicia of deception on a aggregate basis (e.g. occurrence metrics for multiple indicia of deception types, such as eye movement, formal language, etc. are combined into a single indicator for an "overall" view of the indicia of deception) or on an indicia-by-indicia basis (e.g. each indicia type is represented by a separate visual indicator 119).

Further, it will be noted that certain eye movements may be indicia of deception. For example, in the case of a right-handed person, movement of the eyes to the up and left may be indicative of a "constructed" response which may be indicative of deception. Conversely, movement of the eyes up and to the right may be indicative of a "memory recall" response which may be indicative of truthfulness. The above referenced conventions may be reversed for a left-handed person.

As such, the communications content transmitting system 100 may further include a user input device 121 (e.g. a keyboard, mouse, touch pad, touch screen, etc.) that may receive a user input from the content-generating participant 103 defining a "handedness" of the content-generating participant 103. The visual indicator 119 may be displayed on the deceptive indicia display device 118 according to the "handedness" of the content-generating participant 103 so that the act of looking at the visual indicator 119 by the content-generating participant 103 during a communications interaction is not, itself, an indicia of deception. Specifically, for a right-handed content-generating participant 103, the visual indicator 119 may be displayed on the right-hand side of the deceptive indicia display device 118. For a left-handed content-generating participant 103, the visual indicator 119 may be displayed on the left-hand side of the deceptive indicia display device 118 (not shown).

In another embodiment, the upon the receipt of one or more signals associated with the presence of indicia of deception in communications content 102 from the deceptive indicia detection module 113, the deceptive indicia notification module 116 may provide one or more audio signals to a deceptive indicia broadcast device 122 (e.g. an audio speaker, headset, earpiece, etc.) that an audio indicator (e.g. a notification sound effect such as a beep, a spoken message, etc.) associated with the indicia of deception is emitted to the content-generating participant 103.

In order to avoid presenting indicia of deception that rises to a level where it may be detectable by the content-receiving participant 109 via the deceptive indicia detection module 115 of communications module 107, the deceptive indicia detection module 113 may maintain two or more threshold values associated with a given indicia of deception in deceptive indicia threshold database 114 so as to provide a notification that a detectable incidence of deception has likely already occurred as well as to provide a predictive notification that an indicia of deception may occur in the future. For example, the first threshold value may be a predictive threshold value indicating that a number or rate of indicia of deception has occurred which rise to a level which is not likely to be a detectable incidence of deception but may be trending towards such a level. The second threshold value may be a detectable threshold value indicating that sufficient number of indicia of deception have been present in communications content 102 that a content-receiving participant 109 may detect it as an incidence of deception.

It may be the case that the deceptive indicia detection module 113 and deceptive indicia notification module 116 may perform deceptive indicia detection and notification in a substantially real-time manner during a communication interaction (e.g. a video conference) between the content-generating participant 103 and the content-receiving participant 109 to allow the content-generating participant 103 to monitor the communications content 102 for indicia of deception. Further, upon completion of a communications interaction, it may be advisable for a content-generating participant 103 to review the communications content 102 and any detected indicia of deception for education and/or training purposes. As such, during a communication interaction, the deceptive indicia detection module 115 may record the communications content 102 and apply one or more tags to the recorded communications content 102 according to detected occurrences of indicia of deception.

For example, during a communication interaction, the deceptive indicia detection module 115 may detect an incidence of indicia of deception. The deceptive indicia detection module 115 may sample a portion of the communications content 102 containing the detected incidence of indicia of deception and store an audio/video file containing the sampled portion of the communications content 102 containing the detected incidence of indicia of deception to a deceptive indicia library database 123. The audio/video file containing the sampled portion of the communications content 102 containing the detected incidence of indicia of deception may be annotated with information regarding the indicia of deception (e.g. the type of indicia of deception, the degree of deception indicated, etc.) to facilitate review of the detected indicia of deception.

In another example, during a communication interaction, the deceptive indicia detection module 115 may detect an incidence of indicia of deception. The deceptive indicia detection module 115 may record the communications content 102 as an audio/video file and apply a graphical element (e.g. a "flag" icon 124) to the audio/video file at a time associated with the detection of an incidence of indicia of deception. The recorded audio/video file containing the graphical element communications content 102 associated with the detected incidence of indicia of deception may be stored to the deceptive indicia library database 123.

In another example, during a communication interaction, the deceptive indicia detection module 115 may detect an incidence of indicia of deception. The deceptive indicia detection module 115 may store a time stamp associated with the detected incidence of the indicia of deception to the deceptive indicia library database 123.

In another example, a content-generating participant 103 may be independently aware of an occurrence of an indicia of deception contained in the communications content 102 (e.g. the content-generating participant 103 knows they have lied about a maximum authorized purchase price during a negotiation). In such a case, the communications content transmitting system 100 may receive a user input via user input device 121 indicative of an occurrence of indicia of deception in the communications content 102. The deceptive indicia detection module 115 may correlate the occurrence of the user input to detected indicia of deception and apply a tag (e.g. an audio/video sample, an insertion of a graphical element, storing a time stamp, etc.) to the communications content 102 according to the user input.

As described above, it may be advisable for a content-generating participant 103 to review the communications content 102 and any detected indicia of deception for education and/or training purposes. As such, following tagging of the communications content 102 according to the detected indicia of deception, the portions of the communications content 102 associated with the tagged indicia of deception may be replayed to the content-generating participant 103. For example, as shown in FIG. 2A, one or more tagged portions of the communications content 102 may be retrieved from the deceptive indicia library database 123 and displayed/broadcasted by the presentation module 117 via a review interface 125. The review interlace 125 may include video playback functionality configured to present the communications content 102 according to the tags. For example, the review interface 125 may allow for the content-generating participant 103 to skip to portions of the communications content 102 associated with the tags. For example, the review interface 125 may provide a "skip to next" user interface element whereby a user input associated with the "skip to next" user interface element causes the review interface 125 to display/broadcast the next instance of the communications content 102 having a tag associated with a detection of indicia of deception.

In addition to providing a notification to the content-generating participant 103 that the communications content 102 provided to the content-receiving participant 109 may include one or more indicia of deception, one or more remedial measures may be taken to modify the communications content 102 to reduce or remove or, alternately, add or enhance indicia of deception within the communications content 102 prior to providing the communications content 102 to the content-receiving participant 109.

As shown in FIG. 1, following detection of indicia of deception in the communications content 102 by the deceptive indicia detection module 113, the communications content 102 may be provided to a deceptive indicia masking module 126. The deceptive indicia masking module 126 may modify the communications content 102 to reduce or remove the detected indicia of deception within the communications content 102 to produce modified communications content 102'.

For example, as shown in FIG. 1, the deceptive indicia detection module 113 may detect one or more indicia of deception (e.g. micro expressions, eye dilation, eye movement, heart rate, blood pressure, perspiration level, breathing rate, voice stress, use of characteristic language, etc.) in the audio/video signals of the communications content 102. The deceptive indicia detection module 113 may provide data associated with the detected indicia of deception along with the original communications content 102 to the deceptive indicia masking module 126. The deceptive indicia masking module 126 may receive the original communications content 102 and the data associated with the detected indicia of deception and modify the detected indicia of deception in the communications content 102 to produce modified communications content 102'.

In an exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 become dilated in response to stress associated with providing deceptive communications content 102. As described above, the deceptive indicia detection module 113 may detect the dilation of the eyes of content-generating participant 103 as an indicia of deception and provide data regarding such detection to the deceptive indicia masking module 126. Upon receipt of such data, the deceptive indicia masking module 126 may modify the communications content 102 to reduce the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the iris and apply such characteristics to pixels associated with the pupil to reduce the apparent size of the pupil of the content-generating participant 103. The modified pixels may be included in modified communications content 102' which may be provided to the content-receiving participant 109.

In another exemplary embodiment, the deceptive indicia masking module 126 may replace one or more frames of video data of the communications content 102 to produce modified video data of the modified communications content 102'. For example, it may be the case that the communications content capture device 101 may capture video communications content 102 from the content-generating participant 103 that includes footage where the content-generating participant 103 exhibits a micro expression response to stress associated with providing deceptive communications content 102. As described above, the deceptive indicia detection module 113 may detect the micro expression by the content-generating participant 103 as indicia of deception and provide data regarding such detection to the deceptive indicia masking module 126. Upon receipt of such data, the deceptive indicia masking module 126 may modify the communications content 102 to reduce the apparent micro expression by the content-generating participant 103 by replacing one or more frames of the video communications content 102 which depict the micro expression with one or more frames which do not depict the micro expression (e.g. frames directly proceeding the frames depicting the micro expression). In the case of such frame replacement, a content-receiving participant 109 may merely view the repeated frames as a transmission buffering error and not a masking of the micro expression.

In another exemplary embodiment, the deceptive indicia masking module 126 may reduce the resolution on video data of the communications content 102 to produce modified video data of the modified communications content 102'. For example, it may be the case that the communications content capture device 101 may capture video communications content 102 including an indicia of deception from the content-generating participant 103 in a resolution (e.g. 1080p video resolution) high enough that the content-receiving participant 109 may easily detect the presence of indicia of deception in the communications content 102. As described above, the deceptive indicia detection module 113 may detect the indicia of deception in the content-generating participant 103 and provide data regarding such detection to the deceptive indicia masking module 126. Upon receipt of such data, the deceptive indicia masking module 126 may modify the communications content 102 to reduce the apparent indicia of deception by the content-generating participant 103 by reducing the resolution of a portion of the video communications content 102 which depicts the indicia of deception to a resolution (e.g. to 720p, 480i, etc.) which makes the indicia of deception more difficult to detect by the content-receiving participant 109. Specifically, the indicia of deception may be the dilation of the eyes of the content-generating participant 103. Reducing the resolution of the communications content 102 associated with dilation of the eyes of the content-generating participant 103 may result in modified communications content 102' where the display characteristics of pixels associated with the iris and pixels associated with the pupil of content-generating participant 103 become difficult to distinguish.

In another exemplary embodiment, the deceptive indicia masking module 126 may reduce the frame rate of video data of the communications content 102 to produce modified video data of the modified communications content 102'. For example, it may be the case that the communications content capture device 101 may capture video communications content 102 from the content-generating participant 103 that includes footage where the content-generating participant 103 exhibits a micro expression response to stress associated with providing deceptive communications content 102. As described above, the deceptive indicia detection module 113 may detect the micro expression by the content-generating participant 103 as indicia of deception and provide data regarding such detection to the deceptive indicia masking module 126. Upon receipt of such data, the deceptive indicia masking module 126 may modify the communications content 102 to reduce the apparent micro expression by the content-generating participant 103 by reducing the frame rate of the communications content 102 which depict the micro expression such that the a frame duration is greater than the duration of the micro expression.

In another exemplary embodiment, the deceptive indicia masking module 126 may modify the frequency of audio data of the communications content 102 to produce modified audio data of the modified communications content 102'. For example, it may be the case that the communications content capture device 101 may capture audio communications content 102 from the content-generating participant 103 that includes inaudible changes that result from unconscious tensing of the vocal cords resulting in a dampening of selected frequency variations in response to stress associated with providing deceptive communications content 102. Still further, infrasonic, or subsonic, frequency modulation may be present, in some degree, in both the vocal cord sounds and in the formant sounds (e.g. between 8 and 12 Hz). As described above, the deceptive indicia detection module 113 may detect such sounds by content-generating participant 103 as indicia of deception and provide data regarding such detection to the deceptive indicia masking module 126. Upon receipt of such data, the deceptive indicia masking module 126 may reduce the apparent indicia of deception by modifying the audio characteristics (e.g. the frequency, pitch, volume, amplitude, etc.) of the communications content 102 which exhibit indicia of deception to reduce such indicia.

In another exemplary embodiment, the deceptive indicia masking module 126 may apply a filter to audio data of the communications content 102 to produce modified audio data of the modified communications content 102'. For example, it may be the case that the communications content capture device 101 may capture audio communications content 102 from the content-generating participant 103 that includes inaudible changes that result from unconscious tensing of the vocal cords resulting in a dampening of selected frequency variations in response to stress associated with providing deceptive communications content 102. Still further, infrasonic, or subsonic, frequency modulation may be present, in some degree, in both the vocal cord sounds and in the formant sounds (e.g. between 8 and 12 Hz). As described above, the deceptive indicia detection module 113 may detect such sounds by content-generating participant 103 as indicia of deception and provide data regarding such detection to the deceptive indicia masking module 126. Upon receipt of such data, the deceptive indicia masking module 126 may apply a filter to the portions of audio communications content 102 which exhibit indicia of deception to remove such characteristic frequencies.

In another exemplary embodiment, the deceptive indicia masking module 126 may replace one or more portions of the audio/video data of the communications content 102 to produce modified audio/video data of the modified communications content 102'. For example, it may be the case that the communications content capture device 101 may capture audio communications content 102 from the content-generating participant 103 where the content-generating participant 103 employs characteristic language in his or her speech in response to stress associated with providing deceptive communications content 102. As described above, the deceptive indicia detection module 113 may detect the use of formal language by the content-generating participant 103 as indicia of deception and provide data regarding such detection to the deceptive indicia masking module 126. Upon receipt of such data, the deceptive indicia masking module 126 may modify the communications content 102 to reduce the apparent use of formal language by the content-generating participant 103 by replacing one or more frames of the audio/video communications content 102 including the formal language with one or more frames which do not include the formal language. Specifically, the content-generating participant 103 may pre-record portions of the communications content 102 which do not include formal language which may be stored as audio/video files and such stored files may be retrieved and substituted for one or more frames of the communications content 102 that include the formal language upon a detection of the use of such formal language in the communications content 102.

In another exemplary embodiment, the communications content capture device 101 may include a high-resolution camera. The high-resolution camera may image one or more external features of the content-generating participant 103 during capture of the communications content 102. As described above, the deceptive indicia detection module 113 may receive signals associated with the image of the facial region and detect the locations of one or more facial features. Pupil dilation may be measured (e.g. by pixel counts, reflectivity fluctuations, brightness, color, etc. in the facial region image) and monitored for changes over time. Upon detection of a computed pupil dilation in excess of the deceptive indicia threshold value by the deceptive indicia detection module 113, a signal indicative of such detection may be provided to the deceptive indicia masking module 126. The deceptive indicia masking module 126 may modify the communications content 102 to reduce the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the iris and apply such characteristics to pixels associated with the pupil to reduce the apparent size of the pupil of the content-generating participant 103. The modified pixels may be included in modified communications content 102' which may be provided to the content-receiving participant 109.

In another exemplary embodiment, the high-resolution camera may image one or more external features of the content-generating participant 103 during capture of the communications content 102. As described above, the deceptive indicia detection module 113 may receive signals associated with the image of the facial region and detect the locations of one or more facial features. Eye movement may be measured (e.g. by pixel counts, reflectivity fluctuations, brightness, color, etc. in the facial region image) and monitored for changes over time. Upon detection of a computed eye movement in excess of the deceptive indicia threshold value by the deceptive indicia detection module 113 (e.g., in the case of a right-handed person, movement of the eyes to the up and left may be indicative of a "constructed" response which may be indicative of deception), a signal indicative of such detection may be provided to the deceptive indicia masking module 126. The deceptive indicia masking module 126 may modify the communications content 102 to reduce the apparent movement of the eyes of the content-generating participant 103. Specifically, the deceptive indicia masking module 126 may replace pixels representative of the eyes of the content-generating participant 103 which reflect excessive eye movement with pixels representative of the eyes of the content-generating participant 103 which do not include such excessive eye movement.

In an exemplary embodiment, the high-resolution camera image may include sufficient resolution to image the movement of one or more blood vessels (e.g. the external carotid artery, external jugular vein, superficial temporal artery, etc.) of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate for the content-generating participant 103. The computed heart rate may be compared to a deceptive indicia threshold value maintained in the deceptive indicia threshold database 127. As an elevated heart rate may be an indicator of stress associated with providing deceptive communications content 102, a computed heart rate in excess of the deceptive indicia threshold value may be detected as indicia of deception in the communications content 102. The deceptive indicia masking module 126 may modify the communications content 102 to reduce the apparent movements of the blood vessel of the content-generating participant 103. Specifically, the deceptive indicia masking module 126 may replace pixels representative of the blood vessel of the content-generating participant 103 which reflect an excessive heart rate with pixels representative of the blood vessel of the content-generating participant 103 which do not reflect such an excessive heart rate.

Alternately, deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102. The deceptive indicia masking module 126 may modify the communications content 102 to reduce the apparent size of the blood vessel of the content-generating participant 103. Specifically, the deceptive indicia masking module 126 may replace pixels representative of the blood vessel of the content-generating participant 103 which reflect an excessive blood pressure with pixels representative of the blood vessel of the content-generating participant 103 which do not reflect such an excessive blood pressure.

In another exemplary embodiment, the high-resolution camera may image the skin surface of the content-generating participant 103. The deceptive indicia detection module 113 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102. The deceptive indicia masking module 126 may modify the communications content 102 to reduce the apparent size of the perspiration pores or perspiration droplets of the content-generating participant 103. Specifically, the deceptive indicia masking module 126 may replace pixels representative of the perspiration pores or perspiration droplets of the content-generating participant 103 which reflect excessive perspiration with pixels representative of the perspiration pores or perspiration droplets of the content-generating participant 103 which do not reflect such excessive perspiration.

In another exemplary embodiment, the high-resolution camera may image the skin surface of the content-generating participant 103. The deceptive indicia detection module 113 may receive signals associated with the image of the content-generating participant 103 and detect the locations of one or more bodily features. The relative positions of such bodily features may be measured (e.g. pixel counts in the skin surface image) and monitored for changes over time. For example, movement of various bodily features (e.g. the expansion and contraction of the chest cavity, movement of the shoulders, etc.) may be indicative of respiration. As an elevated level of rate of respiration may be an indicator of stress associated with providing deceptive communications content 102, a computed breathing rate in excess of the deceptive indicia threshold value (e.g. a breathing rate) may be detected as indicia of deception in the communications content 102. The deceptive indicia masking module 126 may modify the communications content 102 to reduce the apparent breathing rate of the content-generating participant 103. Specifically, the deceptive indicia masking module 126 may replace pixels representative of the movement of the chest and/or shoulders of the content-generating participant 103 which reflect excessive breathing with pixels representative of the movement of the chest and/or shoulders of the content-generating participant 103 which do not reflect such excessive breathing.

In another exemplary embodiment, the high-resolution camera may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception. Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102. The deceptive indicia masking module 126 may modify the communications content 102 to reduce the apparent micro expression of the content-generating participant 103. Specifically, the deceptive indicia masking module 126 may replace pixels representative of the movement of the eyes, mouth, or other facial features of the content-generating participant 103 which reflect a micro expression with pixels representative of the movement of the eyes, mouth, or other facial features of the content-generating participant 103 which do not reflect such a micro expression.

In another exemplary embodiment, the deceptive indicia detection module 113 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 113 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102. The deceptive indicia masking module 126 may modify the communications content 102 to alter the apparent speaking rate, volume, voice tremor, spacing between syllables, and fundamental pitch or frequency of the voice of the content-generating participant 103. Specifically, the deceptive indicia masking module 126 may introduce delay or apply one or more filters to the voice content of the content-generating participant 103 which reflect voice-changes occurring as a result of stress associated with providing deceptive content with voice content of the content-generating participant 103 which do not reflect such voice-changes occurring as a result of stress associated with providing deceptive content.

In another exemplary embodiment, the deceptive indicia detection module 113 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 113 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102. The deceptive indicia masking module 126 may modify the communications content 102 to alter the language presented by of the content-generating participant 103. Specifically, the deceptive indicia masking module 126 may replace language content of the content-generating participant 103 which reflect formal language with language content of the content-generating participant 103 which do not reflect such formal language by substituting one or more pre-recorded audio files which do not contain the formal language for the portions of the communications content 102 that do contain the formal language.

Further, it may be the case that the content-generating participant 103 wishes to insert false indicia of deception into the communications content 102 in order to further confuse the content-receiving participant 109 with respect to the veracity of the communications content 102. For example, as shown in FIG. 1, the deceptive indicia masking module 126 may modify the communications content 102 at pseudo random intervals to add or enhance indicia of deception within the communications content 102 to produce modified communications content 102'. This modified communications content 102' may be provided to the content-receiving participant 109 in place of communications content 102.

In an exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 have a normal dilation indicative of an absence of stress associated with providing deceptive communications content 102. The deceptive indicia masking module 126 may modify the communications content 102 to increase the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the pupil and apply such characteristics to pixels associated with the iris to increase the apparent size of the pupil of the content-generating participant 103 thereby creating a false indicia of deception. The modified pixels may be included in modified communications content 102' which may be provided to the content-receiving participant 109.

In another exemplary embodiment, the deceptive indicia masking module 126 may replace one or more frames of video data of the communications content 102 to produce modified video data of the modified communications content 102'. For example, it may be the case that the communications content capture device 101 may capture video communications content 102 from the content-generating participant 103 that includes footage where the content-generating participant 103 does not exhibit a micro expression response due to an absence of stress associated with providing deceptive communications content 102. The deceptive indicia masking module 126 may modify the communications content 102 to introduce an apparent micro expression by the content-generating participant 103 by replacing one or more frames of the video communications content 102 which do not depict a micro expression with one or more frames which do depict a micro expression. For example, a pre-recorded video segment including a micro expression of the content-generating participant 103 may be substituted into the communications content 102 in place of portions of the communications content 102 which do not include such a micro expression.

In another exemplary embodiment, the deceptive indicia masking module 126 may modify the modifying the audio characteristics (e.g. the frequency, pitch, volume, amplitude, etc.) of audio data of the communications content 102 to produce modified audio data of the modified communications content 102'. For example, it may be the case that the communications content capture device 101 may capture audio communications content 102 from the content-generating participant 103 that does not include inaudible changes that result from unconscious tensing of the vocal cords resulting in a dampening of selected frequency variations in response to stress associated with providing deceptive communications content 102 (e.g. infrasonic, or subsonic, frequency modulation may be present, in some degree, in both the vocal cord sounds and in the formant sounds (e.g. between 8 and 12 Hz)). The deceptive indicia masking module 126 may introduce apparent indicia of deception by modifying the audio characteristics (e.g. the frequency, pitch, volume, amplitude, etc.) of the communications content 102 which do not exhibit indicia of deception.

In another exemplary embodiment, the deceptive indicia masking module 126 may apply a filter to audio data of the communications content 102 to produce modified audio data of the modified communications content 102'. For example, it may be the case that the communications content capture device 101 may capture audio communications content 102 from the content-generating participant 103 that does not include inaudible changes that result from unconscious tensing of the vocal cords resulting in a dampening of selected frequency variations in response to stress associated with providing deceptive communications content 102 (e.g. infrasonic, or subsonic, frequency modulation may be present, in some degree, in both the vocal cord sounds and in the formant sounds (e.g. between 8 and 12 Hz)). The deceptive indicia masking module 126 may apply a filter to the portions of audio communications content 102 which do not exhibit indicia of deception to add such characteristic frequencies.

In another exemplary embodiment, the communications content capture device 101 may include a high-resolution camera. The high-resolution camera may image one or more external features of the content-generating participant 103 during capture of the communications content 102. The deceptive indicia masking module 126 may modify the communications content 102 to increase the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the pupil and apply such characteristics to pixels associated with the iris to increase the apparent size of the pupil of the content-generating participant 103. The modified pixels may be included in modified communications content 102' which may be provided to the content-receiving participant 109.

In another exemplary embodiment, the high-resolution camera may image one or more external features of the content-generating participant 103 during capture of the communications content 102. The deceptive indicia masking module 126 may modify the communications content 102 to introduce an apparent movement of the eyes of the content-generating participant 103. Specifically, the deceptive indicia masking module 126 may replace pixels representative of the eyes of the content-generating participant 103 which reflect normal eye position with pixels representative of the eyes of the content-generating participant 103 which include such excessive eye movement.

In an exemplary embodiment, the high-resolution camera image may include sufficient resolution to image the movement of one or more blood vessels (e.g. the external carotid artery, external jugular vein, superficial temporal artery, etc.) of the content-generating participant 103. The deceptive indicia masking module 126 may modify the communications content 102 to increase the apparent movements of the blood vessel of the content-generating participant 103. Specifically, the deceptive indicia masking module 126 may replace pixels representative of the blood vessel of the content-generating participant 103 which reflect normal heart rate with pixels representative of the blood vessel of the content-generating participant 103 which exhibit an elevated heart rate.

Alternately, deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel. The deceptive indicia masking module 126 may modify the communications content 102 to increase the apparent size of the blood vessel of the content-generating participant 103. Specifically, the deceptive indicia masking module 126 may replace pixels representative of the blood vessel of the content-generating participant 103 which reflect normal blood pressure with pixels representative of the blood vessel of the content-generating participant 103 which exhibit an elevated blood pressure.

In another exemplary embodiment, the high-resolution camera may image the skin surface of the content-generating participant 103. The deceptive indicia detection module 113 may receive signals associated with the image of the skin surface and detect the locations of one or more skin surface features, such as perspiration pores. The deceptive indicia masking module 126 may modify the communications content 102 to increase the apparent size of the perspiration pores or perspiration droplets of the content-generating participant 103. Specifically, the deceptive indicia masking module 126 may replace pixels representative of the perspiration pores or perspiration droplets of the content-generating participant 103 which reflect normal perspiration with pixels representative of the perspiration pores or perspiration droplets of the content-generating participant 103 which reflect elevated perspiration.

In another exemplary embodiment, the high-resolution camera may image the skin surface of the content-generating participant 103. The deceptive indicia detection module 113 may receive signals associated with the image of the content-generating participant 103 and detect the locations of one or more bodily features. The relative positions of such bodily features may be measured (e.g. pixel counts in the skin surface image) and monitored for changes over time. For example, movement of various bodily features (e.g. the expansion and contraction of the chest cavity, movement of the shoulders, etc.) may be indicative of respiration. The deceptive indicia masking module 126 may modify the communications content 102 to increase the apparent breathing rate of the content-generating participant 103. Specifically, the deceptive indicia masking module 126 may replace pixels representative of the movement of the chest and/or shoulders of the content-generating participant 103 which reflect normal breathing with pixels representative of the movement of the chest and/or shoulders of the content-generating participant 103 which reflect an elevated breathing rate.

In another exemplary embodiment, the high-resolution camera may image the facial region of the content-generating participant 103. The deceptive indicia detection module 113 may receive signals associated with the image of the facial region and detect the locations of one or more facial features. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency), the deceptive indicia masking module 126 may modify the communications content 102 to introduce an apparent micro expression in the content-generating participant 103. Specifically, the deceptive indicia masking module 126 may replace pixels representative of the eyes, mouth, or other facial features of the content-generating participant 103 which do not reflect a micro expression with pixels representative of the movement of the eyes, mouth, or other facial features of the content-generating participant 103 which do reflect such a micro expression.

In another exemplary embodiment, the deceptive indicia detection module 113 may obtain a voice print of speech by the content-generating participant 103. Various types of voice-change may occur as a result of stress associated with providing deceptive communications content 102. The deceptive indicia masking module 126 may modify the communications content 102 to alter the apparent speaking rate, volume, voice tremor, spacing between syllables, and fundamental pitch or frequency of the voice of the content-generating participant 103. Specifically, the deceptive indicia masking module 126 may introduce delay or apply one or more filters to normal voice content of the content-generating participant 103 which do not reflect voice-changes occurring as a result of stress associated with providing deceptive content to generate voice content of the content-generating participant 103 that reflect voice-changes occurring as a result of stress associated with providing deceptive content.

In another exemplary embodiment, the deceptive indicia detection module 113 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 113 may detect the speech terms used in the communications content 102 and measure one or more language usage parameters (e.g. the frequency of use of formal language, the proximity of one formal language instance to the next, etc.). The deceptive indicia masking module 126 may modify the communications content 102 to alter the language presented by of the content-generating participant 103. Specifically, the deceptive indicia masking module 126 may replace language content of the content-generating participant 103 which does not reflect formal language with language content of the content-generating participant 103 which does reflect formal language by substituting one or more pre-recorded audio/video files which contain the formal language for the portions of the communications content 102 that do not contain the formal language.

Further, it may be the case that the content-receiving participant 109 wishes to determine the presence of indicia of deception in the communications content 102 and receive notification thereof. As such, the communications content receiving system 106 may include a deceptive indicia detection module 115 maintaining a deceptive indicia threshold database 127, a deceptive indicia notification module 128, a presentation module 108 and a deceptive indicia library database 129 employing functionality similar to the deceptive indicia detection module 113, deceptive indicia notification module 116, presentation module 117 and deceptive indicia library database 123 described above to detect and notify the content-receiving participant 109 of the presence of indicia of deception in the communications content 102 as well as generate an indicia of deception profile for the content-generating participant 103 to be stored in deceptive indicia library database 129.

For example, as shown in FIG. 1, communications content 102 received by the communications content receiving system 106 from the communications content transmitting system 100 via the communications module 107 may be provided to the deceptive indicia detection module 115 for analysis of the communications content 102 to determine if the communications content 102 represents an indicia of deception. For example, the audio and/or video of the communications content 102 may be analyzed to determine the various physiological characteristics such as heart rate, blood pressure, breathing patterns, perspiration levels as well as other parameters such as eye dilation, eye movements, voice stress, language constructs, and the like of the content-generating participant 103.

Upon receipt of the communications content 102 from the communications content transmitting system 100, such data may be analyzed for correspondence with one or more defined deceptive indicia threshold values maintained in the deceptive indicia threshold database 127. Exceeding one or more deceptive indicia threshold values may be an indicator that the content-generating participant 103 is presenting one or more physiological indicators, speech patterns and/or physical movements that may be associated with deception in the communications content 102.

In an exemplary embodiment, the communications content capture device 101 may include a high-resolution camera (e.g. a camera having a resolution of at least 720 lines in a vertical direction). A high-resolution camera image may include sufficient resolution to image the movement of one or more blood vessels (e.g. the external carotid artery, external jugular vein, superficial temporal artery, etc.) of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate for the content-generating participant 103. The computed heart rate may be compared to a deceptive indicia threshold value maintained in the deceptive indicia threshold database 127. As an elevated heart rate may be an indicator of stress associated with providing deceptive communications content 102, a computed heart rate in excess of the deceptive indicia threshold value may be detected as indicia of deception in the communications content 102.

Alternately, deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

In another exemplary embodiment, the high-resolution camera may image the skin surface of the content-generating participant 103. The deceptive indicia detection module 115 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the high-resolution camera may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

Further, certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

In another exemplary embodiment, the communications content capture device 101 may include a microphone. The microphone may capture an audio signal (e.g. speech content, a voice print, breathing, ambient noise, etc.) of the content-generating participant 103. The deceptive indicia detection module 115 may then analyze the audio signal and detect one or more characteristics of the audio signal.

For example, the deceptive indicia detection module 115 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 115 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

In a further example, the deceptive indicia detection module 115 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 115 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

In a case where a content-generating participant 103 is presenting one or more indicia of deception (e.g. physiological indicators, speech patterns and/or physical movements) that may be interpreted/detected by a content-receiving participant 109 (e.g. detected by the deceptive indicia detection module 115 associated with the communications content receiving system 106) as being associated with deception, it may be desirable for the content-receiving participant 109 to be made aware of such indicia of deception so that the content-receiving participant 109 may account for such deception in considering the communications content 102.

As such, the communications content receiving system 106 may include a deceptive indicia notification module 128. The deceptive indicia notification module 128 may receive one or more signals from the deceptive indicia detection module 115 indicating the presence or absence of deceptive indicia in communications content 102 being provided to the content-receiving participant 109. Upon the receipt of one or more signals associated with the presence of indicia of deception in communications content 102 from the deceptive indicia detection module 115, the deceptive indicia notification module 128 may, in turn provide one or more signals to a presentation module 108 so that an indicator associated with the indicia of deception is presented to the content-receiving participants 109.

Figure 3A:
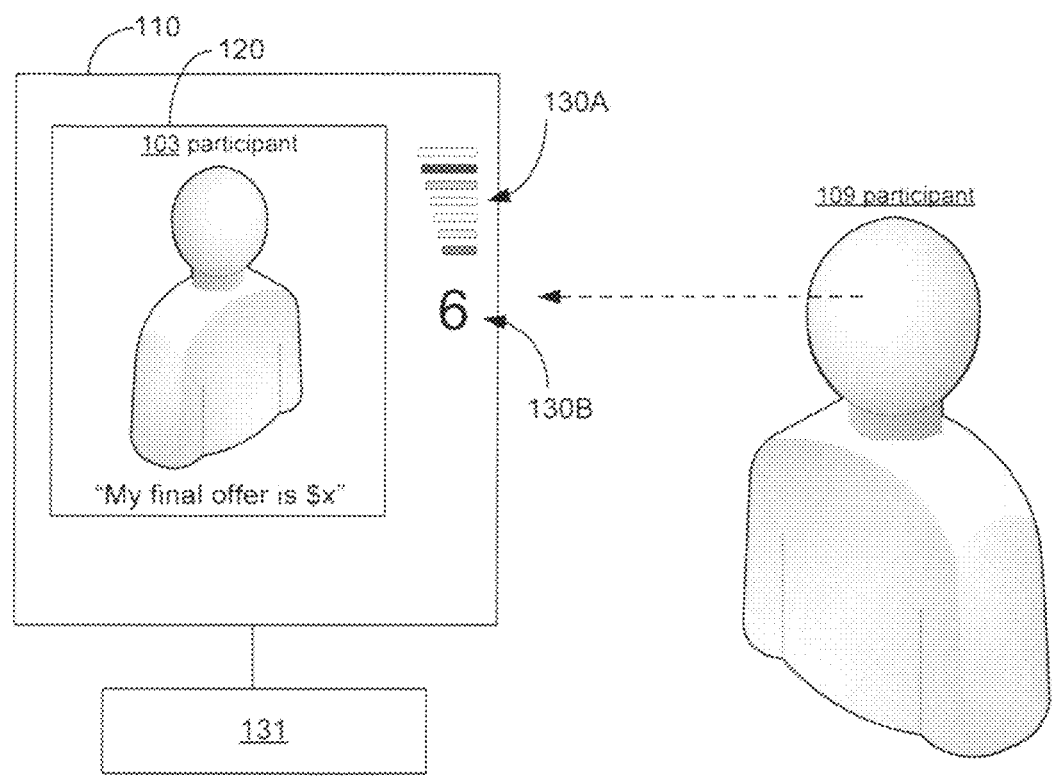
FIG. 3B shows an exemplary high-level block diagram of an exemplary system.

For example, upon the receipt of one or more signals associated with the presence of indicia of deception in communications content 102 from the deceptive indicia detection module 115, the deceptive indicia notification module 128 may provide one or more video signals to a display device 110 (e.g. an LCD display) so that a visual indicator 130 associated with the indicia of deception is presented within a field of view of the content-generating participant 103. As shown in FIG. 3A, the display device 110 may display a video conferencing interface 120 configured to present audio/video content to the content-receiving participant 109 during a communication interaction (e.g. at least one of audio and visual communication between at least the content-generating participant 103 and content-receiving participant 109). The display device 110 may display a visual indicator 130A that presents a rate of occurrences of indicia of deception in the communications content 102, a visual indicator 130B that presents a cumulative number of occurrences of indicia of deception in the communications content 102, a color coded visual indicator 130A (e.g. "green" level indicating a low rate of occurrences of indicia of deception, a "yellow" level indicating a moderate rate of occurrences of indicia of deception, to a "red" level indicating a high rate of occurrences of indicia of deception). The visual indicator 130 may be a dynamic indicator that changes (e.g. moves from an indicated "high" rate of indicia of deception to an indicated "low" rate of indicia of deception) in real-time according to the type and/or amount of indicia of deception detected within communications content 102. The visual indicator 130 may provide an indication of the level of indicia of deception on a aggregate basis (e.g. occurrence metrics for multiple indicia of deception types, such as eye movement, formal language, etc. are combined into a single indicator for an "overall" view of the indicia of deception) or on an indicia-by-indicia basis (e.g. each indicia type is represented by a separate visual indicator 130).

Further, it will be noted that certain eye movements may be indicia of deception. For example, in the case of a right-handed person, movement of the eyes to the up and left may be indicative of a "constructed" response which may be indicative of deception. Conversely, movement of the eyes up and to the right may be indicative of a "memory recall" response which may be indicative of truthfulness. The above referenced conventions may be reversed for a left-handed person.

As such, the communications content receiving system 106 may further include a user input device 131 (e.g. a keyboard, mouse, touch pad, touch screen, etc.) that may receive a user input from the content-receiving participant 109 defining a "handedness" of the content-receiving participant 109. The visual indicator 130 may be displayed on the display device 110 according to the "handedness" of the content-receiving participant 109 so that the act of looking at the visual indicator 130 by the content-receiving participant 109 during a communications interaction is not, itself, an indicia of deception by the content-receiving participant 109. Specifically, for a right-handed content-receiving participant 109, the visual indicator 130 may be displayed on the right-hand side of the display device 110. For a left-handed content-receiving participant 109, the visual indicator 130 may be displayed on the left-hand side of the display device 110 (not shown).

In another embodiment, the upon the receipt of one or more signals associated with the presence of indicia of deception in communications content 102 from the deceptive indicia detection module 115, the deceptive indicia notification module 128 may provide one or more audio signals to a audio speaker 111 (e.g. an audio speaker, headset, earpiece, etc.) that an audio indicator (e.g. a notification sound effect such as a beep, a spoken message, etc.) associated with the indicia of deception is emitted to the content-receiving participant 109.

In order to provide predictive detection of indicia of deception, the deceptive indicia detection module 115 may maintain two or more threshold values associated with a given indicia of deception in deceptive indicia threshold database 127 so as to provide a notification that a detectable incidence of deception has likely already occurred as well as to provide a predictive notification that an indicia of deception may occur in the future. For example, the first threshold value may be a predictive threshold value indicating that a number or rate of indicia of deception has occurred which rise to a level which is not likely to be a detectable incidence of deception but may be trending towards such a level. The second threshold value may be a detectable threshold value indicating that sufficient number of indicia of deception have been present in communications content 102 that a content-receiving participant 109 may detect it as an incidence of deception.

It may be the case that the deceptive indicia detection module 115 and deceptive indicia notification module 128 may perform deceptive indicia detection and notification in a substantially real-time manner during a communication interaction (e.g. a video conference) between the content-generating participant 103 and the content-receiving participant 109 to allow the content-receiving participant 109 to monitor the communications content 102 for indicia of deception. Further, upon completion of a communications interaction, it may be advisable for a content-receiving participant 109 to review the communications content 102 and any detected indicia of deception for education and/or training purposes. As such, during a communication interaction, the deceptive indicia detection module 115 may record the communications content 102 and apply one or more tags to the recorded communications content 102 according to detected occurrences of indicia of deception.

For example, during a communication interaction, the deceptive indicia detection module 115 may detect an incidence of indicia of deception. The deceptive indicia detection module 115 may sample a portion of the communications content 102 containing the detected incidence of indicia of deception and store an audio/video file containing the sampled portion of the communications content 102 containing the detected incidence of indicia of deception to a deceptive indicia library database 129. The audio/video file containing the sampled portion of the communications content 102 containing the detected incidence of indicia of deception may be annotated with information regarding the indicia of deception (e.g. the type of indicia of deception, the degree of deception indicated, etc.) to facilitate review of the detected indicia of deception.

In another example, during a communication interaction, the deceptive indicia detection module 115 may detect an incidence of indicia of deception. The deceptive indicia detection module 115 may record the communications content 102 as an audio/video file and apply a graphical element (e.g. a "flag" icon 132) to the audio/video file at a time associated with the detection of an incidence of indicia of deception. The recorded audio/video file containing the graphical element communications content 102 associated with the detected incidence of indicia of deception may be stored to the deceptive indicia library database 129.

In another example, during a communication interaction, the deceptive indicia detection module 115 may detect an incidence of indicia of deception. The deceptive indicia detection module 115 may store a time stamp associated with the detected incidence of the indicia of deception to the deceptive indicia library database 129.

In another example, a content-receiving participant 109 may be independently aware of an occurrence of an indicia of deception contained in the communications content 102 (e.g. the content-receiving participant 109 knows the content-generating participant 103 has lied about a maximum authorized purchase price during a negotiation). In such a case, the communications content receiving system 106 may receive a user input via user input device 131 indicative of an occurrence of indicia of deception in the communications content 102. The deceptive indicia detection module 115 may correlate the occurrence of the user input to detected indicia of deception and apply a tag (e.g. an audio/video sample, an insertion of a graphical element, storing a time stamp, etc.) to the communications content 102 according to the user input.

Figure 3B:
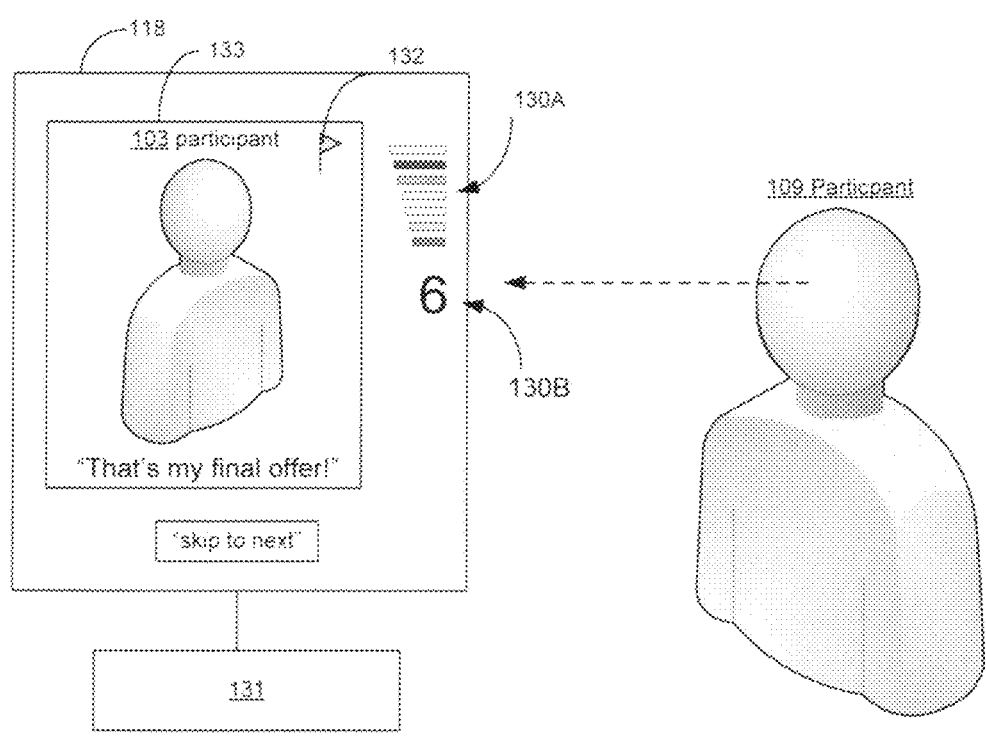

As described above, it may be advisable for a content-receiving participant 109 to review the communications content 102 and any detected indicia of deception for education and/or training purposes. As such, following tagging of the communications content 102 according to the detected indicia of deception, the portions of the communications content 102 associated with the tagged indicia of deception may be replayed to the content-receiving participant 109. For example, as shown in FIG. 3B, one or more tagged portions of the communications content 102 may be retrieved from the deceptive indicia library database 129 and displayed/broadcasted by the presentation module 108 via a review interface 133. The review interface 133 may include video playback functionality configured to present the communications content 102 according to the tags. For example, the review interface 133 may allow for the content-receiving participant 109 to skip to portions of the communications content 102 associated with the tags. For example, the review interface 133 may provide a "skip to next" user interface element whereby a user input associated with the "skip to next" user interface element causes the review interface 133 to display/broadcast the next instance of the communications content 102 having a tag associated with a detection of indicia of deception.

Further, it may be the case that the content-receiving participant 109 may suspect that the content-generating participant 103 may be employing indicia of deception masking techniques via deceptive indicia masking module 126. As such, the communications content receiving system 106 may further include a deceptive indicia masking detection module 134. The deceptive indicia masking detection module 134 may receive modified communications content 102' and detect whether or not deceptive indicia masking has been applied to the original communications content 102. Upon detection of one or more instances of deceptive indicia masking by the deceptive indicia masking detection module 134, the deceptive indicia masking detection module 134 may remove the instances of the deceptive indicia masking from the modified communications content 102' to restore the original communications content 102 and provide the original communications content 102 and/or a notification that deceptive indicia masking has been detected to the content-receiving participant 109 via the presentation module 108.

For example, as shown in FIG. 1, communications content 102 generated by the content-generating participant 103 may be provided to a deceptive indicia masking module 126. The deceptive indicia masking module 126 may modify the communications content 102 to reduce or remove indicia of deception within the communications content 102 to produce modified communications content 102'. In an exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 become dilated in response to stress associated with providing deceptive communications content 102. As described above, the deceptive indicia detection module 113 may detect the dilation of the eyes of content-generating participant 103 as an indicia of deception and provide data regarding such detection to the deceptive indicia masking module 126. Upon receipt of such data, the deceptive indicia masking module 126 may modify the communications content 102 to reduce the apparent dilation of the eyes of content-generating participant 103 by modifying (e.g. altering the color, brightness, contrast, etc.) one or more pixels of the image associated with the pupil and/or iris.

Following modification of the communications content 102 to generate the modified communications content 102', it may be the case that the modified communications content 102' is provided to the content-receiving participant 109. Audio and/or video signals associated with the modified communications content 102' may be transmitted by the communications content transmitting system 100 to the communications content receiving system 106 where the modified communications content 102' is received by the communications module 107. As described above, it may the case that content-receiving participant 109 may have reason to believe that the content-generating participant 103 may provide communications content 102 which could include indicia of deception and, as such, the content-generating participant 103 may employ deceptive indicia masking module 126 to modify the communications content 102 to reduce or remove the indicia of deception in the communications content 102. As such, the modified communications content 102' may be routed to the deceptive indicia masking detection module 134 to analyze the modified communications content 102' to detect indicia of modification in the modified communications content 102'. For example, the deceptive indicia masking detection module 134 may detect two or more repeated (e.g. identical) video frames in the modified communications content 102'. As such repeated frames may be indicative of a modification in the modified communications content 102' by the deceptive indicia masking module 126, the deceptive indicia masking detection module 134 may detect such repeated frames as an indicia of modification in the modified communications content 102'.

In another exemplary embodiment, the communications content capture device 101 may include a high-resolution camera (e.g. a camera having a resolution of at least 720 lines in a vertical direction). A high-resolution camera may image the movements of the content-generating participant 103. The images may be modified by the deceptive indicia masking module 126 as described above and provided as modified communications content 102' to the communications content receiving system 106 where they may be received by the deceptive indicia masking detection module 134 for analysis of the existence of indicia of modification of the modified communications content 102'.

In another exemplary embodiment, the communications content capture device 101 may include a microphone. The microphone may capture an audio signal (e.g. speech content, a voice print, breathing, ambient noise, etc.) of the content-generating participant 103. The audio signals may be modified by the deceptive indicia masking module 126 as described above and provided as modified communications content 102' to the communications content receiving system 106 where they may be received by the deceptive indicia masking detection module 134 for analysis of the existence of indicia of modification of the modified communications content 102'.

In another exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 become dilated in response to stress associated with providing deceptive communications content 102. The deceptive indicia masking module 126 may modify the communications content 102 to reduce the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the iris and apply such characteristics to pixels associated with the pupil to reduce the apparent size of the pupil of the content-generating participant 103. The modified pixels may be included in modified communications content 102' which may be provided to the content-receiving participant 109. Upon receipt of the modified communications content 102', the deceptive indicia masking detection module 134 may analyze the modified communications content 102' for evidence that one or more pixels associated with the dilation of the eyes of the content-generating participant 103 have been modified. For example, the deceptive indicia masking detection module 134 may detect adjacent pixels having identical color, brightness and/or contrast values. Such identical adjacent pixels may be indicative of a replacement of one or more pixels associated with the pupil of the content-generating participant 103 with one or more pixels associated with the iris of the content content-generating participant 103 so as to reduce the apparent dilation of the eyes of the content-generating participant 103.

In another exemplary embodiment, the communications content capture device 101 may capture video communications content 102 from the content-generating participant 103 that includes footage where the content-generating participant 103 exhibits a micro expression response to stress associated with providing deceptive communications content 102. The deceptive indicia masking module 126 may modify the communications content 102 to reduce the apparent micro expression by the content-generating participant 103 by replacing one or more frames of the video communications content 102 which depict the micro expression with one or more frames which do not depict the micro expression (e.g. frames directly proceeding the frames depicting the micro expression). The modified pixels may be included in modified communications content 102' which may be provided to the content-receiving participant 109. Upon receipt of the modified communications content 102', the deceptive indicia masking detection module 134 may analyze the modified communications content 102' for evidence that one or more frames of the modified communications content 102' have been modified. For example, the deceptive indicia masking detection module 134 may detect sequential frames having identical pixels. Such identical sequential frames may be indicative of a replacement of one or more frames containing an indicia of deception with one or more frames lacking an indicia of deception meant to conceal an indicia of deception by the content-generating participant 103. Alternately, the deceptive indicia masking detection module 134 may detect sequential frames having widely varying pixels. Such varying sequential frames may be indicative of a replacement of one or more frames containing an indicia of deception with one or more pre-recorded frames meant to conceal an indicia of deception by the content-generating participant 103. For example, a first frame may indicate the presence of a shadow in the video content while a second frame directly following the first does not include an indication of a shadow.

In another exemplary embodiment, the communications content capture device 101 may capture video communications content 102 including an indicia of deception from the content-generating participant 103 in a resolution (e.g. 1080p video resolution) high enough that the content-receiving participant 109 may easily detect the presence of indicia of deception in the communications content 102. The deceptive indicia masking module 126 may modify the communications content 102 to reduce the apparent indicia of deception by the content-generating participant 103 by reducing the resolution of a portion of the video communications content 102 which depicts the indicia of deception to a resolution (e.g. to 720p, 480i, etc.) which makes the indicia of deception more difficult to detect by the content-receiving participant 109. Upon receipt of the modified communications content 102', the deceptive indicia masking detection module 134 may analyze the modified communications content 102' for evidence that the resolution of the modified communications content 102' have been modified. For example, the deceptive indicia masking detection module 134 may detect that a portion of the modified communications content 102' has a resolution different than that of other portions of the modified communications content 102'. Such resolution differences may be indicative of an induced resolution degradation meant to conceal an indicia of deception by the content-generating participant 103.

In another exemplary embodiment, the communications content capture device 101 may capture video communications content 102 from the content-generating participant 103 that includes footage where the content-generating participant 103 exhibits a micro expression in response to stress associated with providing deceptive communications content 102. The deceptive indicia masking module 126 may modify the communications content 102 to reduce the apparent micro expression by the content-generating participant 103 by reducing the frame rate of the portion of the communications content 102 which depicts the micro expression such that a frame duration is greater than the duration of the micro expression. Upon receipt of the modified communications content 102', the deceptive indicia masking detection module 134 may analyze the modified communications content 102' for evidence that the frame rate of the modified communications content 102' have been modified. For example, the deceptive indicia masking detection module 134 may detect that a portion of the modified communications content 102' has a frame rate different than that of other portions of the modified communications content 102'. Such frame rate differences may be indicative of an induced frame rate modification meant to conceal an indicia of deception by the content-generating participant 103.

In another exemplary embodiment, the communications content capture device 101 may capture audio communications content 102 from the content-generating participant 103 that includes inaudible changes that result from unconscious tensing of the vocal cords resulting in a dampening of selected frequency variations in response to stress associated with providing deceptive communications content 102. Still further, infrasonic, or subsonic, frequency modulation may be present, in some degree, in both the vocal cord sounds and in the formant sounds (e.g. between 8 and 12 Hz). The deceptive indicia masking module 126 may reduce the apparent indicia of deception by modifying the audio characteristics (e.g. the frequency, pitch, volume, amplitude, etc.) of the communications content 102 which exhibit indicia of deception to reduce such indicia. Upon receipt of the modified communications content 102', the deceptive indicia masking detection module 134 may analyze the modified communications content 102' for evidence that one or more audio characteristics of the modified communications content 102' have been modified. For example, the deceptive indicia masking detection module 134 may detect that a portion of the modified communications content 102' has a frequency, pitch, volume, amplitude different than that of other portions of the modified communications content 102'. Such audio characteristic differences may be indicative of an induced audio characteristic modification meant to conceal indicia of deception by the content-generating participant 103. Such divergent audio characteristics may be indicative of a replacement of one or more portions containing an indicia of deception with one or more pre-recorded frames lacking an indicia of deception meant to conceal the indicia of deception by the content-generating participant 103. For example, a first portion may indicate the presence of background audio content (e.g. automobile traffic) while a second portion directly following the first does not include the background audio content.

In another exemplary embodiment the deceptive indicia masking detection module 134 may detect that a portion of the modified communications content 102' has a frequency, pitch, volume, amplitude different than that of other portions of the modified communications content 102'. Such divergent audio characteristics may be indicative of a replacement of one or more portions containing an indicia of deception with one or more pre-recorded frames lacking an indicia of deception meant to conceal the indicia of deception by the content-generating participant 103. For example, a first portion may indicate the presence of background audio content (e.g. automobile traffic) while a second portion directly following the first does not include the background audio content.

In another exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 become dilated in response to stress associated with providing deceptive communications content 102. The deceptive indicia masking module 126 may modify the communications content 102 to reduce the apparent dilation of the eyes of content-generating participant 103 by modifying (e.g. altering the color, brightness, contrast, etc.) one or more pixels of the image associated with the pupil and/or iris. Specifically, the deceptive indicia masking module 126 may sample the characteristics of the pixels of the image associated with the iris and apply such characteristics to pixels associated with the pupil to reduce the apparent size of the pupil of the content-generating participant 103. The modified pixels may be included in modified communications content 102' which may be provided to the content-receiving participant 109. Upon receipt of the modified communications content 102', the deceptive indicia masking detection module 134 may analyze the modified communications content 102' for evidence that one or more pixels associated with the dilation of the eyes of the content-generating participant 103 have been modified. For example, the deceptive indicia masking detection module 134 may detect adjacent pixels having identical color, brightness and/or contrast values. Such identical adjacent pixels may be indicative of a replacement of one or more pixels associated with the pupil of the content-generating participant 103 with one or more pixels associated with the iris of the content content-generating participant 103 so as to reduce the apparent dilation of the eyes of the content-generating participant 103.

In another exemplary embodiment, the deceptive indicia masking module 126 may modify one or more pixels of the video data of the communications content 102 to produce modified video data of the modified communications content 102'. For example, it may be the case that the communications content capture device 101 may capture video communications content 102 from the content-generating participant 103 that includes footage where the eyes of the content-generating participant 103 move in response to stress associated with providing deceptive communications content 102 (e.g., in the case of a right-handed person, movement of the eyes to the up and left may be indicative of a "constructed" response which may be indicative of deception). The deceptive indicia masking module 126 may modify the communications content 102 to reduce the apparent movement of the eyes of content-generating participant 103 by modifying (e.g. altering the color, brightness, contrast, etc.) one or more pixels of the image associated with the pupil and/or iris. Specifically, the deceptive indicia masking module 126 may replace pixels representative of the eyes of the content-generating participant 103 which reflect excessive eye movement with pixels representative of the eyes of the content-generating participant 103 which do not include such excessive eye movement. The modified pixels may be included in modified communications content 102' which may be provided to the content-receiving participant 109. Upon receipt of the modified communications content 102', the deceptive indicia masking detection module 134 may analyze the modified communications content 102' for evidence that one or more pixels associated with the movement of the eyes of the content-generating participant 103 have been modified. For example, the deceptive indicia masking detection module 134 may detect incongruities between the location of the eyes of content-generating participant 103 between sequential frames of video content of the modified communications content 102'. Such incongruities between sequential may be indicative of a replacement of one or more frames associated with the eyes of the content-generating participant 103 so as to reduce the apparent movement of the eyes of the content-generating participant 103.

In another exemplary embodiment, the communications content capture device 101 may image the movement of one or more blood vessels (e.g. the external carotid artery, external jugular vein, superficial temporal artery, etc.) of the content-generating participant 103. The deceptive indicia detection module 113. The deceptive indicia masking module 126 may modify the communications content 102 to alter the apparent timing of the movements of the blood vessel of the content-generating participant 103. Specifically, the deceptive indicia masking module 126 may replace pixels representative of the blood vessel of the content-generating participant 103 which reflect an excessive heart rate with pixels representative of the blood vessel of the content-generating participant 103 which do not reflect such an excessive heart rate. Upon receipt of the modified communications content 102', the deceptive indicia masking detection module 134 may analyze the modified communications content 102' for evidence that one or more pixels associated with the heart rate of the content-generating participant 103 have been modified. For example, the deceptive indicia masking detection module 134 may detect incongruities between the locations of the blood vessels of content-generating participant 103 between sequential frames of video content of the modified communications content 102'. Such incongruities between sequential frames may be indicative of a replacement of one or more frames associated with the blood vessel of the content-generating participant 103 so as to reduce the apparent heart rate of the content-generating participant 103.

In another exemplary embodiment, the communications content capture device 101 may image the size of one or more blood vessels (e.g. the external carotid artery, external jugular vein, superficial temporal artery, etc.) of the content-generating participant 103. The deceptive indicia detection module 113. The deceptive indicia masking module 126 may modify the communications content 102 to reduce the apparent size of the blood vessel of the content-generating participant 103. Specifically, the deceptive indicia masking module 126 may replace pixels representative of the blood vessel of the content-generating participant 103 which reflect an excessive heart rate with pixels representative of the blood vessel of the content-generating participant 103 which do not reflect such an excessive blood pressure. Upon receipt of the modified communications content 102', the deceptive indicia masking detection module 134 may analyze the modified communications content 102' for evidence that one or more pixels associated with the blood pressure of the content-generating participant 103 have been modified. For example, the deceptive indicia masking detection module 134 may detect incongruities between the locations of the blood vessels of content-generating participant 103 between sequential frames of video content of the modified communications content 102'. Such incongruities between sequential frames may be indicative of a replacement of one or more frames associated with the blood vessel of the content-generating participant 103 so as to reduce the apparent blood pressure of the content-generating participant 103.

In another exemplary embodiment, the communications content capture device 101 may image the skin surface and detect the locations of one or more skin surface features, such as perspiration pores. The deceptive indicia masking module 126 may modify the communications content 102 to reduce the apparent size of the perspiration pores and/or perspiration droplets of the content-generating participant 103. Specifically, the deceptive indicia masking module 126 may replace pixels representative of the perspiration pores and/or perspiration droplets of the content-generating participant 103 which reflect excessive perspiration with pixels representative of the perspiration pores or perspiration droplets of the content-generating participant 103 which do not reflect such excessive perspiration. Upon receipt of the modified communications content 102', the deceptive indicia masking detection module 134 may analyze the modified communications content 102' for evidence that one or more pixels associated with the perspiration pores and/or perspiration droplets of the content-generating participant 103 have been modified. For example, the deceptive indicia masking detection module 134 may detect incongruities between the locations of the perspiration pores and/or perspiration droplets of content-generating participant 103 between sequential frames of video content of the modified communications content 102'. Such incongruities between sequential frames may be indicative of a replacement of one or more frames associated with the perspiration pores and/or perspiration droplets of the content-generating participant 103 so as to reduce the apparent perspiration level of the content-generating participant 103.

In another exemplary embodiment, the communications content capture device 101 may image locations of one or more bodily features. The deceptive indicia masking module 126 may modify the communications content 102 to reduce the apparent breathing rate of the content-generating participant 103. Specifically, the deceptive indicia masking module 126 may replace pixels representative of the movement of the chest and/or shoulders of the content-generating participant 103 which reflect excessive breathing with pixels representative of the movement of the chest and/or shoulders of the content-generating participant 103 which do not reflect such excessive breathing. Upon receipt of the modified communications content 102', the deceptive indicia masking detection module 134 may analyze the modified communications content 102' for evidence that one or more pixels associated with the breathing of the content-generating participant 103 have been modified. For example, the deceptive indicia masking detection module 134 may detect incongruities between the locations of the chest and/or shoulders of content-generating participant 103 between sequential frames of video content of the modified communications content 102'. Such incongruities between sequential frames may be indicative of a replacement of one or more frames associated with the chest and/or shoulders of the content-generating participant 103 so as to reduce the apparent breathing rate of the content-generating participant 103.

In another exemplary embodiment, the deceptive indicia masking module 126 may modify the communications content 102 to reduce the apparent micro expression of the content-generating participant 103. Specifically, the deceptive indicia masking module 126 may replace pixels representative of the movement of the eyes, mouth, or other facial features of the content-generating participant 103 over a threshold duration of time which reflect a micro expression with pixels representative of the movement of the eyes, mouth, or other facial features of the content-generating participant 103 which do not reflect such a micro expression. Upon receipt of the modified communications content 102', the deceptive indicia masking detection module 134 may analyze the modified communications content 102' for evidence that one or more pixels associated with the movement of the eyes, mouth, or other facial features of the content-generating participant 103 have been modified. For example, the deceptive indicia masking detection module 134 may detect incongruities between the locations of the movement of the eyes, mouth, or other facial features of content-generating participant 103 between sequential frames of video content of the modified communications content 102'. Such incongruities between sequential frames may be indicative of a replacement of one or more frames associated with the movement of the eyes, mouth, or other facial features of the content-generating participant 103 so as to reduce the appearance of micro expressions of the content-generating participant 103.

In another exemplary embodiment, the deceptive indicia masking module 126 may modify the communications content 102 to reduce the apparent voice stress of the content-generating participant 103 by altering the apparent speaking rate, volume, voice tremor, spacing between syllables, and fundamental pitch or frequency of the voice of the content-generating participant 103. Specifically, the deceptive indicia masking module 126 may introduce delay or apply one or more filters to the voice content of the content-generating participant 103 which reflect voice-changes occurring as a result of stress associated with providing deceptive content with voice content of the content-generating participant 103 which do not reflect such voice-changes occurring as a result of stress associated with providing deceptive content. Upon receipt of the modified communications content 102', the deceptive indicia masking detection module 134 may analyze the modified communications content 102' for evidence that one or more segments of the audio content from the content-generating participant 103 have been modified. For example, the deceptive indicia masking detection module 134 may detect incongruities between the timing of audio content and video content of the modified communications content 102' (e.g. movements of the mouth of the content-generating participant 103 in the video content do not match the simultaneous audio content. Such incongruities between the timing of audio content and video content of the modified communications content 102' may be indicative of a replacement of audio content of the content-generating participant 103 so as to reduce the appearance of micro expressions of the content-generating participant 103.

In another exemplary embodiment, various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "But I thought . . . "), lack of antecedent basis for an article ("A man approached me and pointed a gun at me. He stuck the gun in my ribs and forced me into the car" where no prior reference to "a car" had been made), and the like. The deceptive indicia masking module 126 may modify the communications content 102 to alter the language presented by of the content-generating participant 103. Specifically, the deceptive indicia masking module 126 may replace language content of the content-generating participant 103 which reflect formal language with language content of the content-generating participant 103 which do not reflect such formal language by substituting one or more pre-recorded audio files which do not contain the formal language for the portions of the communications content 102 that do contain the formal language. Upon receipt of the modified communications content 102', the deceptive indicia masking detection module 134 may analyze the modified communications content 102' for evidence that one or more segments of the audio content from the content-generating participant 103 have been modified. For example, the deceptive indicia masking detection module 134 may detect that a portion of the modified communications content 102' has a frequency, pitch, volume, amplitude different than that of other portions of the modified communications content 102'. Such audio characteristic differences may be indicative of an induced audio characteristic modification meant to conceal indicia of deception by the content-generating participant 103. Such divergent audio characteristics may be indicative of a replacement of one or more portions containing an indicia of deception with one or more pre-recorded frames lacking an indicia of deception meant to conceal the indicia of deception by the content-generating participant 103. For example, a first portion may indicate the presence of background audio content (e.g. automobile traffic) while a second portion directly following the first does not include the background audio content.

In another exemplary embodiment, upon the receipt of one or more signals associated with a detection of an indicia of a modification in the modified communications content 102' from the deceptive indicia masking detection module 134, the deceptive indicia notification module 128 may provide one or more video signals to a display device 110 (e.g. an LCD display) so that a visual indicator 130 associated with the detection of an indicia of a modification in the modified communications content 102' is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display the visual indicator 130 (e.g. a color coded indicator) that presents a cumulative number of occurrences of detection of an indicia of a modification in the modified communications content 102', a rate of occurrences of a detection of an indicia of a modification in the modified communications content 102', and the like. The visual indicator 130 may be a dynamic indicator that changes (e.g. moves from an indicated "high" rate of indicia of deception to an indicated "low" rate of indicia of deception) in real-time according to the type and/or amount of detection of indicia of modification in the modified communications content 102'.

In another exemplary embodiment, upon the receipt of one or more signals associated with a detection of an indicia of a modification in the modified communications content 102' from the deceptive indicia masking detection module 134, the deceptive indicia notification module 128 may provide one or more video signals to a display device 110 (e.g. an LCD display) so that a visual indicator 130 associated with the detection of an indicia of a modification in the modified communications content 102' is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display the visual indicator 130 (e.g. a color coded indicator) that presents a cumulative number of occurrences of detection of an indicia of a modification in the modified communications content 102', a rate of occurrences of a detection of an indicia of a modification in the modified communications content 102', and the like. The visual indicator 130 may be a dynamic indicator that changes (e.g. moves from an indicated "high" rate of indicia of a modification in the modified communications content 102' to an indicated "low" rate of indicia of a modification in the modified communications content 102') in real-time according to the type and/or amount of detection of indicia of modification in the modified communications content 102'.

In another exemplary embodiment, upon the receipt of one or more signals associated with a detection of an indicia of a modification in the modified communications content 102' from the deceptive indicia masking detection module 134, the deceptive indicia notification module 128 may provide one or more video signals to a display device 110 (e.g. an LCD display) so that a visual indicator 130 associated with the detection of an indicia of a modification in the modified communications content 102' is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display a visual indicator 130 that presents a cumulative number of occurrences of detection of indicia of modification in the modified communications content 102'.

In another exemplary embodiment, upon the receipt of one or more signals associated with a detection of an indicia of a modification in the modified communications content 102' from the deceptive indicia masking detection module 134, the deceptive indicia notification module 128 may provide one or more video signals to a display device 110 (e.g. an LCD display) so that a visual indicator 130 associated with the detection of an indicia of a modification in the modified communications content 102' is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display a visual indicator 130 that presents a rate of occurrences of detection of indicia of modification in the modified communications content 102'.

In another exemplary embodiment, upon the receipt of one or more signals associated with the detection of an indicia of a modification in the modified communications content 102' from the deceptive indicia masking detection module 134, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may display a color coded visual indicator 130A (e.g. "green" level indicating a low rate of occurrences of indicia of a modification in the modified communications content 102', a "yellow" level indicating a moderate rate of occurrences of indicia of a modification in the modified communications content 102', to a "red" level indicating a high rate of occurrences of indicia of a modification in the modified communications content 102'). The visual indicator 130A may be a dynamic indicator that changes (e.g. moves from an indicated "high" rate of indicia of a modification in the modified communications content 102' to an indicated "low" rate of indicia of a modification in the modified communications content 102') in real-time according to the type and/or amount of indicia of a modification in the modified communications content 102' detected. Alternately, each indicia of a modification in the modified communications content 102' type may be represented by a separate visual indicator 130 having a designated color. For example, indicia of a modification in the modified communications content 102' associated with eye movement of the content-generating participant 103 may be represented by a blue visual indicator 130 while indicia of a modification in the modified communications content 102' associated with formal language may be represented by a green visual indicator 130.

In another exemplary embodiment, upon the receipt of one or more signals associated with the detection of an indicia of a modification in the modified communications content 102' from the deceptive indicia masking detection module 134, the deceptive indicia notification module 128 may provide one or more audio signals to an audio speaker 111 (e.g. an audio speaker, headset, earpiece, etc.) that an audio indicator (e.g. a notification sound effect such as a beep, a spoken message, etc.) associated with the detection of an indicia of a modification in the modified communications content 102' is emitted to the content-receiving participant 109.

In another exemplary embodiment, it may be the case that the deceptive indicia masking detection module 134 and deceptive indicia notification module 128 may perform modification indicia detection and notification (as described above) in a substantially real-time manner during a communication interaction (e.g. a video conference) between the content-generating participant 103 and the content-receiving participant 109 to allow the content-receiving participant 109 to monitor the communications content 102 for indicia of a modification in the modified communications content 102' and account for such indicia of a modification in the modified communications content 102' in their consideration of the veracity of the modified communications content 102' received from the content-generating participant 103.

In another exemplary embodiment, upon completion of a communications interaction, it may be advisable for a content-receiving participant 109 to review the modified communications content 102' and any detected indicia of modification for education and/or training purposes. During a communication interaction, the deceptive indicia masking detection module 134 may detect an incidence of an indicia of a modification in the modified communications content 102'. The deceptive indicia masking detection module 134 may store a record associated with the detected indicia of a modification in the modified communications content 102' to a deceptive indicia library database 129. Following the communications interaction, one or more portions of the modified communications content 102' may be retrieved from the deceptive indicia library database 129 and displayed/broadcasted by the presentation module 108 via a review interface 133. The review interface 133 may include video playback functionality configured to present the modified communications content 102' according to the records associated with the detected indicia of deception. The review interface 133 may allow for the content-receiving participant 109 to skip to portions of the modified communications content 102' associated with the records associated with the detected indicia of a modification in the modified communications content 102'. For example, the review interface 133 may provide a "skip to next" user interface element whereby a user input associated with the "skip to next" user interface element causes the review interface 133 to display/broadcast the next instance of the modified communications content 102' having a record associated with a detection of indicia of a In another exemplary embodiment, upon completion of a communications interaction, it may be advisable for a content-receiving participant 109 to review the modified communications content 102' and any detected indicia of a modification in the modified communications content 102' for education and/or training purposes. During a communication interaction, the deceptive indicia masking detection module 134 may detect an incidence of indicia of a modification in the modified communications content 102'. The deceptive indicia masking detection module 134 may record the modified communications content 102' and apply one or more tags to the recorded modified communications content 102' according to detected occurrences of indicia of a modification in the modified communications content 102'.

In another exemplary embodiment, during a communication interaction, the deceptive indicia masking detection module 134 may detect indicia of a modification in the modified communications content 102'. The deceptive indicia masking detection module 134 may sample a portion of the modified communications content 102' containing the detected incidence of indicia of a modification in the modified communications content 102' and store an audio/video file containing the sampled portion of the modified communications content 102' containing the detected incidence of indicia of a modification in the modified communications content 102' to a deceptive indicia library database 129. The audio/video file containing the sampled portion of the modified communications content 102' containing the detected incidence of indicia of a modification in the modified communications content 102' may be annotated with information regarding the indicia of a modification in the modified communications content 102' (e.g. the type of indicia of modification, the degree of modification indicated, etc.) to facilitate review of the detected indicia of modification.

In another exemplary embodiment, during a communication interaction, the deceptive indicia masking detection module 134 may detect an incidence of indicia of a modification in the modified communications content 102'. The deceptive indicia masking detection module 134 may record the modified communications content 102' as an audio/video file and apply a graphical element (e.g. a "flag" icon 132) to the audio/video file at a time associated with the detection of the incidence of indicia of a modification in the modified communications content 102'. The recorded audio/video file containing the graphical element communications content 102 associated with the detected incidence of indicia of a modification in the modified communications content 102' may be stored to the deceptive indicia library database 129.

In another exemplary embodiment, during a communication interaction, the deceptive indicia masking detection module 134 may detect an incidence of indicia of a modification in the modified communications content 102'. The deceptive indicia detection module 115 may store a time stamp associated with the detected incidence of the indicia of a modification in the modified communications content 102' to the deceptive indicia library database 129.

In another exemplary embodiment, a content-receiving participant 109 may be independently aware of an occurrence of indicia of a modification in the modified communications content 102' contained in the communications content 102 (e.g. the content-receiving participant 109 knows that the content-generating participant 103 has lied about a maximum authorized purchase price during a negotiation). In such a case, the communications content receiving system 106 may receive a user input (e.g. a keystroke) via user input device 131 indicative of an occurrence of indicia of a modification in the modified communications content 102'. The deceptive indicia masking detection module 134 may correlate the occurrence of the user input to detected indicia of a modification in the modified communications content 102' and apply a tag (e.g. an audio/video sample, an insertion of a graphical element, storing a time stamp, etc.) to the communications content 102 according to the user input.

Still further, it may be the case that multiple content-receiving participants 109 may employ multiple communications content receiving systems 106 to receive communications content 102 from a common content-generating participant 103. In order to generate a more comprehensive indicia of deception profile for the content-generating participant 103, the content-receiving participants 109 may aggregate their respective indicia of deception data in a deceptive indicia repository 135 that is commonly accessible by the content-receiving participants 109. For example, a communications content receiving system 106A and communications content receiving system 106B may be employed by a first content-receiving participant 109A and a second content-receiving participant 109B, respectively, to receive communications content 102 from the content-generating participant 103. The communications content receiving system 106A and communications content receiving system 106B may be substantially similar in that the communications content receiving system 106B may provide all the functionality of communications content receiving system 106A as described herein. Following a communications interaction with the content-generating participant 103, the communications content receiving system 106A and communications content receiving system 106B may upload indicia of deception data associated with one or more communication interactions with the content-generating participant 103 to the deceptive indicia repository 135. Further, each communications content receiving system 106 may download aggregated indicia of deception data associated with multiple communication interactions with the content-generating participant 103 and provide that aggregated indicia of deception data to a content-receiving participant 109 via the presentation module 108 for review by the content-receiving participant 109.

In an exemplary embodiment, the communications content capture device 101 may include, but is not limited to, a video capture device (e.g. a digital camera, web cam, teleconferencing camera, etc.), an audio capture device (e.g. a microphone, telephone), and the like. The communications content 102 received by the communications content receiving system 106A from the communications content transmitting system 100 during a first communications interaction with the content-generating participant 103 may be provided to the deceptive indicia detection module 115A for analysis of the communications content 102 to determine if the communications content 102 represents an indicia of deception. Upon receipt of communications content 102 received from the communications content transmitting system 100, such data may be analyzed by the deceptive indicia detection module 115A for correspondence with one or more defined deceptive indicia threshold values maintained in the deceptive indicia threshold database 127. Exceeding one or more deceptive indicia threshold values may be an indicator that the content-generating participant 103 is presenting one or more physiological indicators, speech patterns and/or physical movements that may be associated with deception in the communications content 102.

In another exemplary embodiment, the communications content capture device 101 may include, but is not limited to, a video capture device (e.g. a digital camera, web cam, teleconferencing camera, etc.), an audio capture device (e.g. a microphone, telephone), and the like. The communications content 102 received by the communications content receiving system 106B from the communications content transmitting system 100 via the communications module 107 may be provided to the deceptive indicia detection module 115 for analysis of the communications content 102 to determine if the communications content 102 represents an indicia of deception. Upon receipt of communications content 102 received from the communications content transmitting system 100, such data may be analyzed by the deceptive indicia detection module 1158 for correspondence with one or more defined deceptive indicia threshold values maintained in the deceptive indicia threshold database 127. Exceeding one or more deceptive indicia threshold values may be an indicator that the content-generating participant 103 is presenting one or more physiological indicators, speech patterns and/or physical movements that may be associated with deception in the communications content 102.

In another exemplary embodiment, following one or more communications interactions with the content-generating participant 103, the deceptive indicia detection module 115 may provide indicia of deception data to the deceptive indicia repository 135 (e.g. a server) maintaining a participant database 136. The participant database 136 may include a participant profile 137 associated with the content-generating participant 103. The participant profile 137 may include information associated with the indicia of deception detected in various communications interactions with the content-generating participant 103. For example, the participant profile 137 may include cumulative and/or exemplary data associated with various types of indicia of deception (e.g. formal language, physical movements, etc.) as well as their frequency as detected in communications content 102 provided by the content-generating participant 103 during communications interactions with the content-receiving participant 109A and/or the content-receiving participant 109B.

In another exemplary embodiment, the high-resolution camera of the communications content capture device 101 may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. Certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

In another exemplary embodiment, the high-resolution camera of the communications content capture device 101 may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time.

In another exemplary embodiment, the high-resolution camera may image the facial region of the content-generating participant 103. The deceptive indicia detection module 115 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

In another exemplary embodiment, the high-resolution camera of the communications content capture device 101 may externally image one or more blood vessels of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate. The computed heart rate may be compared to a deceptive indicia threshold value maintained in the deceptive indicia threshold database 114. As an elevated heart rate may be an indicator of stress associated with providing deceptive communications content 102, a computed heart rate in excess of the deceptive indicia threshold value may be detected as indicia of deception in the communications content 102.

In another exemplary embodiment, the high-resolution camera of the communications content capture device 101 may externally image one or more blood vessels of the content-generating participant 103. The deceptive indicia detection module 115 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

In another exemplary embodiment, the high-resolution camera of the communications content capture device 101 may image the skin surface of the content-generating participant 103. The deceptive indicia detection module 115 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

In another exemplary embodiment, the communications content capture device 101 and/or the physiological data capture device 112 may include a high-resolution camera. The high-resolution camera may image the skin surface of the content-generating participant 103. The deceptive indicia detection module 115 may receive signals associated with the image of the content-generating participant 103 and detect the locations of one or more bodily features. The relative positions of such bodily features may be measured (e.g. pixel counts in the skin surface image) and monitored for changes over time. For example, movement of various bodily features (e.g. the expansion and contraction of the chest cavity, movement of the shoulders, etc.) may be indicative of respiration. As an elevated level of rate of respiration may be an indicator of stress associated with providing deceptive communications content 102, a computed breathing rate in excess of the deceptive indicia threshold value (e.g. a breathing rate) may be detected as indicia of deception in the communications content 102.

In another exemplary embodiment, the deceptive indicia detection module 115 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 115 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

In another exemplary embodiment, the communications content capture device 101 may include a microphone. The microphone may capture speech content of the content-generating participant 103. The deceptive indicia detection module 115 may then analyze the audio signal and detect one or more characteristics of the audio signal. For example, the deceptive indicia detection module 115 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "I thought . . . " instead of "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 115 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

In another exemplary embodiment, the deceptive indicia repository 135 may receive data associated with detected indicia of deception in communications content 102 provided by the content-generating participant 103 in two or more communications interactions with the content-receiving participant 109A and/or the content-receiving participant 109B. The indicia of deception data may be aggregated (e.g. combined, summed, grouped, etc.) according to one or more parameters (e.g. indicia type, date of communication interaction, identity of the content-receiving participant 109, etc.) The aggregated indicia of deception data may be stored to the participant profile 137 associated with the content-generating participant 103.

In another exemplary embodiment, the deceptive indicia repository 135 may receive data associated with detected indicia of deception in communications content 102 provided by the content-generating participant 103 in two or more communications interactions with the content-receiving participant 109A and/or the content-receiving participant 109B. The indicia of deception data may be compared between the two or more communications. For example, indicia of deception associated with the movement of the eyes content-generating participant 103 may be detected in a first communications interaction as well as a second communications interaction. The movement of the eyes of the content-generating participant 103 in the first communications interaction may be compared to the move of the eyes of the content-generating participant 103 in the second communications interaction. The degree of correspondence between the two detected indicia of deception may be used to refine a participant profile characteristic (e.g. a threshold eye movement distance that constitutes an indicia of deception) for the content-generating participant 103. Specifically, if over a period of time the degree of departure from a normalized model that is characteristic of a particular indicia of deception changes, the normalized model and/or the threshold departure required for a detection of an indicia of deception may be modified according to the comparison of indicia of deception data between the two or more communications.

In another exemplary embodiment, the deceptive indicia repository 135 may receive data associated with detected indicia of deception in communications content 102 provided by the content-generating participant 103 in two or more communications interactions with the content-receiving participant 109A and/or the content-receiving participant 109B. The indicia of deception data may be averaged between the two or more communications interactions. For example, indicia of deception associated with the movement of the eyes content-generating participant 103 may be detected in a first communications interaction as well as a second communications interaction. The movement of the eyes of the content-generating participant 103 in the first communications interaction may be averaged with the movement of the eyes of the content-generating participant 103 in the second communications interaction. The average value associated with the respective indicia of deception data may be used to refine a participant profile characteristic (e.g. a threshold eye movement distance, frequency, direction, etc., that constitutes an indicia of deception) for the content-generating participant 103. Specifically, the participant profile characteristic may be set as the average of two or more indicia of deception from the two or more communications interactions.

In another exemplary embodiment, the deceptive indicia repository 135 may receive data associated with detected indicia of deception in communications content 102 provided by the content-generating participant 103 in two or more communications interactions with the content-receiving participant 109A and/or the content-receiving participant 109B. The indicia of deception data may be analyzed to determine a frequency of a given indicia of deception within the communications content 102 provided by the content-generating participant 103 in the two or more communications interactions with the content-receiving participant 109A and/or the content-receiving participant 109B. For example, the frequency of the use of formal language may be detected in a first communications interaction as well as a second communications interaction. The frequencies may be may normalized for the length of each communications interaction and an overall frequency may be computed. This overall frequency may be stored to the participant profile 137 associated with the content-generating participant 103 maintained by the deceptive indicia repository 135.

In another exemplary embodiment, the deceptive indicia repository 135 may receive data associated with detected indicia of deception in communications content 102 provided by the content-generating participant 103 in two or more communications interactions with the content-receiving participant 109A and/or the content-receiving participant 109B. The indicia of deception data may be analyzed to determine an exemplary instance of a given indicia of deception within the communications content 102 provided by the content-generating participant 103 in the two or more communications interactions with the content-receiving participant 109A and/or the content-receiving participant 109B. For example, video footage associated with a common micro expression presented in each of the two or more communications interactions may be stored to the participant profile 137 associated with the content-generating participant 103 maintained by the deceptive indicia repository 135.

In another exemplary embodiment, in a case where a content-generating participant 103 is presenting one or more indicia of deception (e.g. physiological indicators, speech patterns and/or physical movements), it may be desirable for the content-receiving participant 109 be made aware of indicia of deception in the communications content 102 so that the content-receiving participant 109 may properly account for such indicia in judging the veracity of the communications content 102. As such, the communications content receiving system 106 may include a deceptive indicia notification module 128. The deceptive indicia notification module 128 may receive one or more signals from the deceptive indicia detection module 115 indicating the presence or absence of deceptive indicia in communications content 102 being provided to the content-receiving participant 109. The presence or absence of deceptive indicia may be determined by comparing the currently detected indicia of deception to stored data associated with one or more indicia of deception detected in a prior communications interaction and stored in the participant profile 137 associated with the content-generating participant 103 maintained by the deceptive indicia repository 135. Upon a determination that a currently detected indicia of deception substantially corresponds to the stored data associated with one or more indicia of deception detected in a prior communications interaction the deceptive indicia detection module 115 may provide one or more signals indicating that the currently detected indicia does or does not correspond to the participant profile 137. Upon the receipt of one or more signals associated with the presence of indicia of deception in communications content 102 from the deceptive indicia detection module 115, the deceptive indicia notification module 128 may, in turn provide one or more signals to a presentation module 108 so that an indicator associated with the indicia of deception is presented to the content-receiving participants 109.

In another exemplary embodiment, a content-receiving participant 109 may provide one or more inputs to user input device 131 to make a selection of one or more types of indicia of deception of interest associated with the content-generating participant 103. The deceptive indicia notification module 128 may retrieve stored indicia of deception data maintained in the participant profile 137 associated with the content-generating participant 103 for display on the display device 110. For example, a content-receiving participant 109 may desire to view detection metrics (e.g. frequency, duration, degree of departure from a normalized model, etc.) associated with of a selected type of indicia of deception (e.g. micro expressions) detected in two or more communications interactions with the content-generating participant 103. The deceptive indicia notification module 128 may retrieve data associated with one or more instances of the selected type of indicia of deception (e.g. the frequency of micro expressions in the two or more communications interactions) and display data for the content-receiving participant 109 on the display device 110.

In another exemplary embodiment, a content-receiving participant 109 may provide one or more inputs to user input device 131 to make a selection of one or more types of indicia of deception of interest associated with the content-generating participant 103. The deceptive indicia notification module 128 may retrieve stored examples of the indicia of deception maintained in the participant profile 137 associated with the content-generating participant 103 for display on the display device 110. For example, a content-receiving participant 109 may desire to view one or more instances of a selected type of indicia of deception (e.g. pupil dilation) detected in two or more communications interactions with the content-generating participant 103. The deceptive indicia notification module 128 may retrieve data associated with one or more instances of the selected type of indicia of deception (e.g. video footage of the micro expressions) and display data for the content-receiving participant 109 on the display device 110.

In another exemplary embodiment, upon the receipt of one or more signals associated with the presence of indicia of deception in communications content 102 from the deceptive indicia detection module 115 as determined according to a comparison with the participant profile 137, the deceptive indicia notification module 128 may provide one or more video signals to a display device 110 (e.g. an LCD display) so that a visual indicator 130 associated with the indicia of deception is presented within a field of view of the content-receiving participant 109. As shown in FIG. 3A, the display device 110 may display a video conferencing interface 120 configured to present audio/video content from the content-generating participant 103 during a communication interaction (e.g. at least one of audio and visual communication between at least the content-generating participant 103 and content-receiving participant 109). The display device 110 may further display the visual indicator 130 (e.g. a color coded indicator) that presents a cumulative number of occurrences of indicia of deception in the communications content 102, a rate of occurrences of indicia of deception in the communications content 102, and the like. The visual indicator 130 may be a dynamic indicator that changes (e.g.

moves from an indicated "high" rate of indicia of deception to an indicated "low" rate of indicia of deception) in real-time according to the type and/or amount of indicia of deception detected within communications content 102.

In another exemplary embodiment, upon the receipt of one or more signals associated with the presence of indicia of deception in communications content 102 from the deceptive indicia detection module 115 as determined according to a comparison with the participant profile 137, the deceptive indicia notification module 128 may provide one or more audio signals to an audio speaker 111 (e.g. an audio speaker, headset, earpiece, etc.) that an audio indicator (e.g. a notification sound effect such as a beep, a spoken message, etc.) associated with the indicia of deception is emitted to the content-receiving participant 109.

In another exemplary embodiment, it may be the case that the deceptive indicia detection module 115 and deceptive indicia notification module 128 may perform deceptive indicia detection and notification (as described above) in a substantially real-time manner during a communication interaction (e.g. a video conference) between the content-generating participant 103 and the content-receiving participant 109 to allow the content-receiving participant 109 to monitor the communications content 102 for indicia of deception and account for such indicia of deception in their consideration of the veracity of the communications content 102 received from the content-generating participant 103.

In another exemplary embodiment, upon completion of a communications interaction, it may be advisable for a content-receiving participant 109 to review the communications content 102 and any detected indicia of deception for education and/or training purposes. During a communication interaction, the deceptive indicia detection module 115 may detect an incidence of indicia of deception. The deceptive indicia detection module 115 may store a record associated with the detected indicia of deception to a deceptive indicia library database 129. Following the communications interaction, one or more portions of the communications content 102 may be retrieved from the deceptive indicia library database 129 and displayed/broadcasted by the presentation module 108 via a review interface 133. The review interface 133 may include video playback functionality configured to present the communications content 102 according to the records associated with the detected indicia of deception. The review interface 133 may allow for the content-generating participant 103 to skip to portions of the communications content 102 associated with the records associated with the detected indicia of deception. For example, the review interface 133 may provide a "skip to next" user interface element whereby a user input associated with the "skip to next" user interface element causes the review interface 133 to display/broadcast the next instance of the communications content 102 having a record associated with a detection of indicia of deception.

Still further, it may be the case that a content-generating participant 103 may engage in multiple communications interactions with one or more content-receiving participants 109. In order to generate a more comprehensive indicia of deception profile for the content-generating participant 103 to facilitate optimizing deceptive indicia detection in content generated by the content-generating participant 103, the communications content transmitting system 100 may aggregate indicia of deception data from multiple communications interactions with one or more content-receiving participants 109 in the deceptive indicia library database 123. For example, the content-generating participant 103 may engage in a first communications interaction with a first content-receiving participant 109A via a first communications content receiving system 106A and a second communications interaction with a second content-receiving participant 109B via a first communications content receiving system 106B. The deceptive indicia detection module 113 may detect one or more indicia of deception in both the first communications interaction and the second communications interaction. The data associated with the indicia of deception in both the first communications interaction and the second communications interaction may be individually stored to a deceptive indicia library database 123. Following the accumulation of two or more samples of data associated with the indicia of deception, the deceptive indicia detection module 113 may retrieve data associated with the two or more instances of data associated with indicia of deception from the deceptive indicia library database 123 and iteratively optimize a deceptive indicia threshold value associated with the indicia of deception maintained in the deceptive indicia threshold database 114. For example, the various instances of data associated with an indicia of deception may be averaged or used to determine minimum and maximum variations of the indicia of deception to more closely reflect the indicia of deception characteristics of the content-generating participant 103. In this manner, the communications content transmitting system 100 may "learn" based on the indicia of deception data stored to the deceptive indicia threshold database 114 to further refine deceptive indicia detection threshold values used by the deceptive indicia detection module 113 in detection of indicia of deception by the content-generating participant 103.

Figure 4:
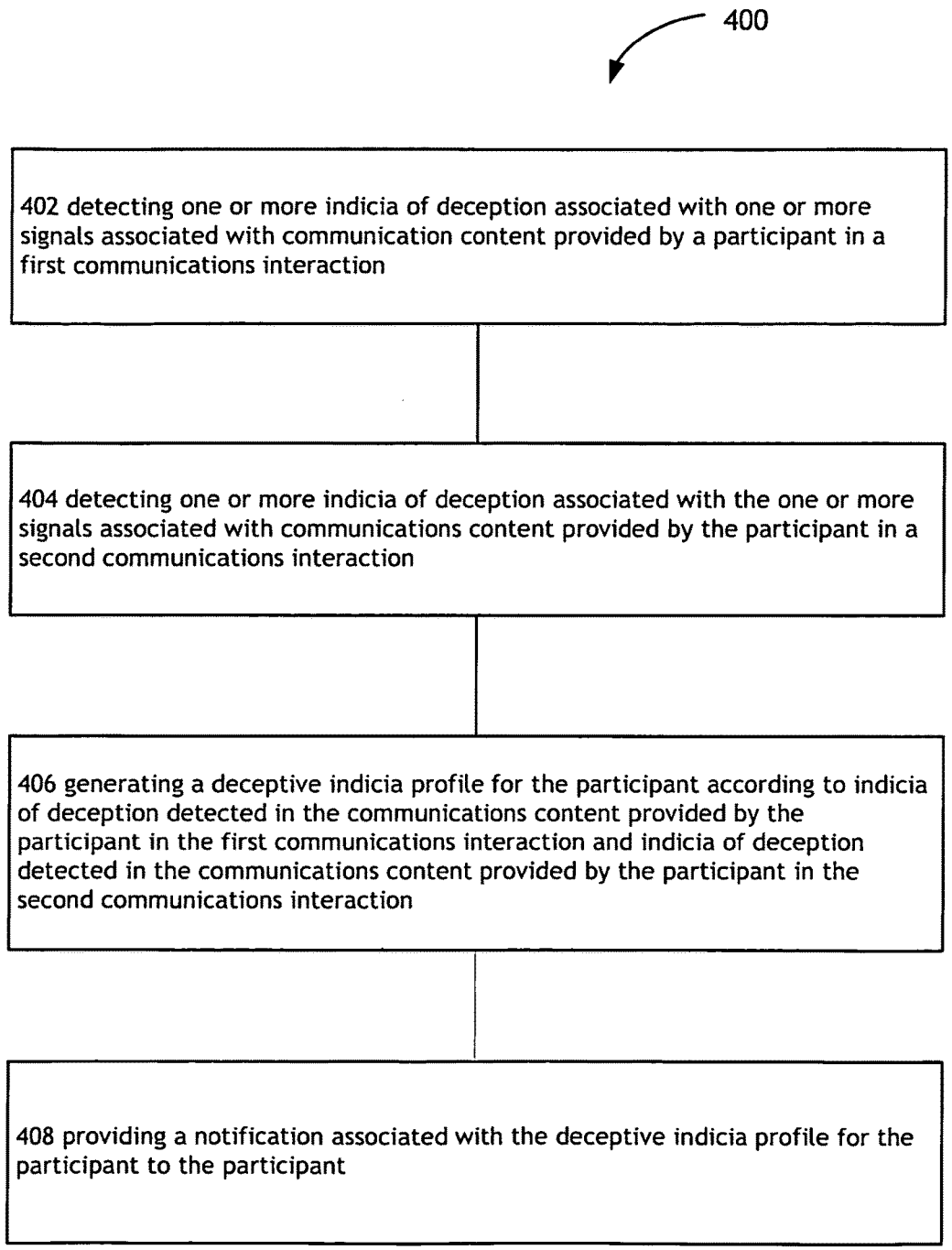
FIG. 4 shows an operational procedure.

FIG. 4 and the following figures include various examples of operational flows, discussions and explanations may be provided with respect to the above-described exemplary environment of FIGS. 1-3B. However, it should be understood that the operational flows may be executed in a number of other environments and contexts, and/or in modified versions of FIGS. 1-3B. In addition, although the various operational flows are presented in the sequence(s) illustrated, it should be understood that the various operations may be performed in different sequential orders other than those which are illustrated, or may be performed concurrently.

Further, in the following figures that depict various flow processes, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

FIG. 4 illustrates an operational procedure 400 for practicing aspects of the present disclosure including operations 402, 404 and 406.

Operation 402 illustrates detecting one or more indicia of deception associated with one or more signals associated with communication content provided by a participant in a first communications interaction. For example, as shown in FIG. 1, the communications content capture device 101 may include, but is not limited to, a video capture device (e.g. a digital camera, web cam, teleconferencing camera, etc.), an audio capture device (e.g. a microphone, telephone), and the like. The communications content 102 received from the content-generating participant 103 by the communications content capture device 101 of the communications content transmitting system 100 during a first communications interaction with a first content-receiving participant 109A may be provided to the deceptive indicia detection module 113 for analysis of the communications content 102 to determine if the communications content 102 represents an indicia of deception. Upon receipt of communications content 102, such data may be analyzed by the deceptive indicia detection module 113 for correspondence with one or more defined deceptive indicia threshold values maintained in the deceptive indicia threshold database 114. Exceeding one or more deceptive indicia threshold values may be an indicator that the content-generating participant 103 is presenting one or more physiological indicators, speech patterns and/or physical movements that may be associated with deception in the communications content 102.

Operation 404 illustrates detecting one or more indicia of deception associated with one or more signals associated with communications content provided by the participant in a second communications interaction. For example, as shown in FIG. 1, the communications content capture device 101 may include, but is not limited to, a video capture device (e.g. a digital camera, web cam, teleconferencing camera, etc.), an audio capture device (e.g. a microphone, telephone), and the like. The communications content 102 received from the content-generating participant 103 by the communications content capture device 101 of the communications content transmitting system 100 during a second communications interaction with a second content-receiving participant 109B may be provided to the deceptive indicia detection module 113 for analysis of the communications content 102 to determine if the communications content 102 represents an indicia of deception. Upon receipt of communications content 102, such data may be analyzed by the deceptive indicia detection module 113 for correspondence with one or more defined deceptive indicia threshold values maintained in the deceptive indicia threshold database 114. Exceeding one or more deceptive indicia threshold values may be an indicator that the content-generating participant 103 is presenting one or more physiological indicators, speech patterns and/or physical movements that may be associated with deception in the communications content 102. Data indicative of a detection of such indicia of deception may be stored to the deceptive indicia library database 123.

Operation 406 illustrates generating a deceptive indicia profile for the participant according to indicia of deception detected in the communications content provided by the participant in the first communications interaction and indicia of deception detected in the communications content provided by the participant in the second communications interaction. For example, as shown in FIG. 1, following two or more communications interactions by the content-generating participant 103, the deceptive indicia detection module 113 may retrieve indicia of deception data associated with at least the first and second communications interactions with the content-receiving participant 109A and/or the content-receiving participant 109B from the deceptive indicia library database 123. The deceptive indicia detection module 113 analyze the various instances of indicia of deception data associated with the content-generating participant 103 to generate a deceptive indicia profile 138 for the content-generating participant 103. For example, the deceptive indicia profile 138 may include averaged, cumulative and/or exemplary data associated with various types of indicia of deception (e.g. formal language, physical movements, etc.) as well as their frequency as detected in communications content 102 provided by the content-generating participant 103 during multiple communications interactions with the content-receiving participant 109A and/or the content-receiving participant 109B.

Operation 408 depicts providing a notification associated with the deceptive indicia profile for the participant to the participant. For example, as shown in FIGS. 1 and 3A-3B, in a case where a content-generating participant 103 is presenting one or more indicia of deception (e.g. physiological indicators, speech patterns and/or physical movements), it may be desirable for the content-generating participant 103 be made aware of such indicia of deception so that the content-generating participant 103 may take remedial steps to mitigate such indicia in a case where the content-generating participant 103 desires to avoid presenting an indication of deception in the communications content 102, or alternately, introduce indicia of deception into communications content 102 where the content-generating participant 103 desires to present a false indication of deception in the communications content 102.

As such, the communications content receiving system 106 may include a deceptive indicia notification module 116. The deceptive indicia notification module 116 may receive one or more signals from the deceptive indicia detection module 113 indicating the presence or absence of deceptive indicia in communications content 102 being provided to the content-receiving participant 109. The presence or absence of deceptive indicia may be determined by comparing the currently detected indicia of deception to stored data associated with one or more indicia of deception detected in a prior communications interaction and stored in the deceptive indicia profile 138 associated with the content-generating participant 103 maintained by the deceptive indicia threshold database 114. Upon a determination that a currently detected indicia of deception substantially corresponds to the stored deceptive indicia profile 138 computed from one two or more a prior communication interactions, the deceptive indicia detection module 113 may provide one or more signals indicating that the currently detected indicia does or does not correspond to the deceptive indicia profile 138. Upon the receipt of one or more signals associated with the presence of indicia of deception in communications content 102 from the deceptive indicia detection module 113, the deceptive indicia notification module 116 may, in turn provide one or more signals to a presentation module 117 so that an indicator associated with the indicia of deception corresponding to the deceptive indicia profile 138 is presented to the content-receiving participants 109.

Figure 5:
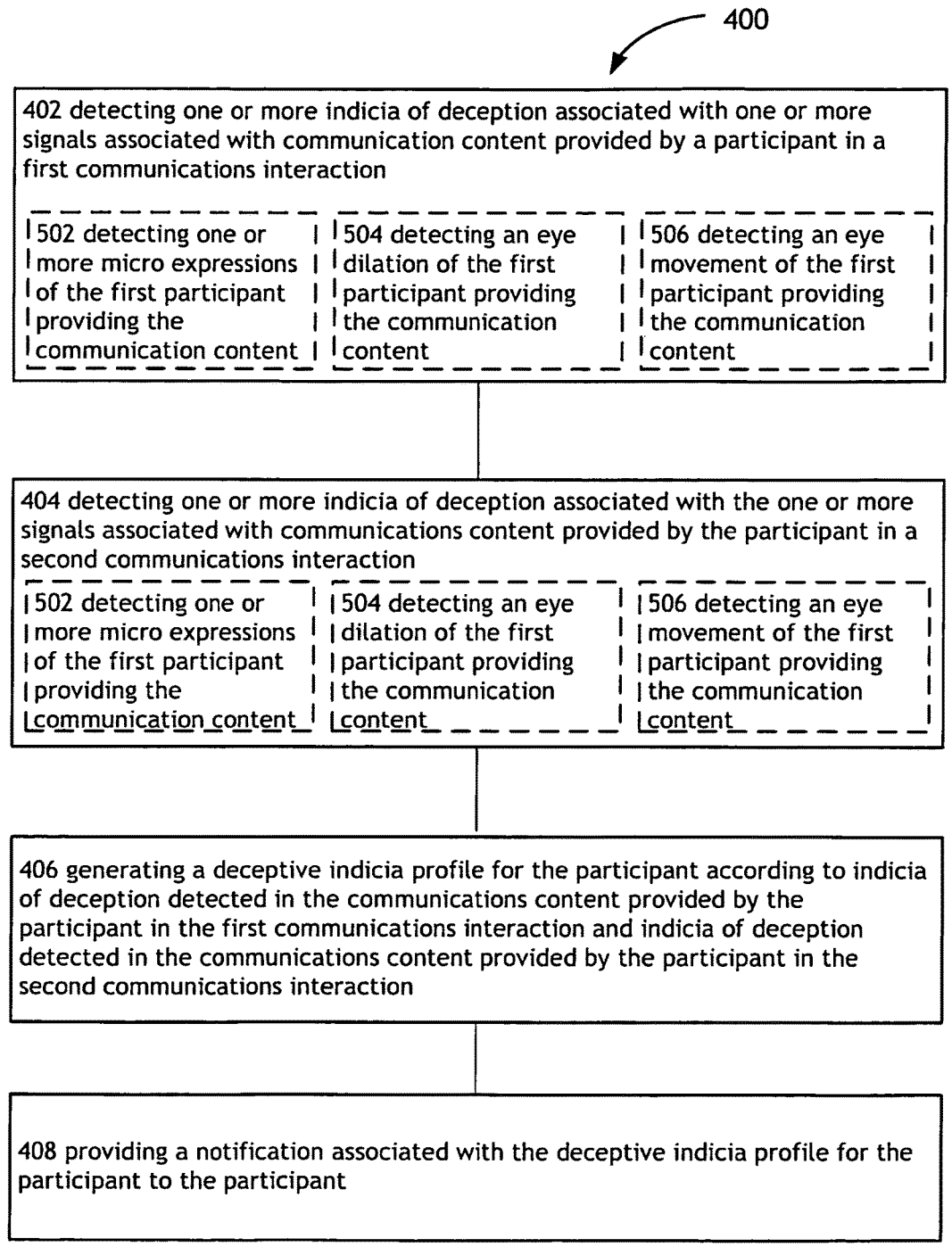
FIG. 5 shows an alternative embodiment of the operational procedure of FIG. 4.

FIG. 5 illustrates an example embodiment where the operations 402 and/or 404 of example operational flow 400 of FIG. 4 may include at least one additional operation. Additional operations may include an operation 502, 504 and/or 506.

Operation 502 illustrates detecting one or more micro expressions of the first participant providing the communication content. For example, as shown in FIG. 1, the high-resolution camera of the communications content capture device 101 may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. Certain brief, involuntary facial movements (e.g. "micro-expressions") may be associated with certain underlying emotions of the content-generating participant 103. For example, the Facial Action Coding System (FACS) developed by Paul Ekman and Wallace Friesen has mapped various facial movements to underlying emotions. As certain physical movements (e.g. pupil dilation, eye movement, micro-expressions, etc.) may be an indicator of deceptive communications content 102, a computed facial movement (e.g. pupil dilation) in excess of the deceptive indicia threshold value (e.g. movement duration, movement distance, movement frequency) may be detected as indicia of deception in the communications content 102.

Operation 504 illustrates detecting an eye dilation of the first participant providing the communication content. For example, as shown in FIG. 1, the high-resolution camera of the communications content capture device 101 may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time.

Operation 506 illustrates detecting an eye movement of the first participant providing the communication content. For example, as shown in FIG. 1, the high-resolution camera may image the facial region of the content-generating participant 103. The deceptive indicia detection module 113 may receive signals associated with the image of the facial region and detect the locations of one or more facial features. The movements of various facial features (e.g. the eyes and, more specifically, pupil dilation) may be measured (e.g. pixel counts, reflectivity fluctuations, brightness, color, etc. in the facial region image) and monitored for changes over time. For example, in the case of a right-handed person, movement of the eyes to the up and left may be indicative of a "constructed" response which may be indicative of deception.

FIG. 6 illustrates an example embodiment where the operations 402 and/or 404 of example operational flow 400 of FIG. 4 may include at least one additional operation. Additional operations may include an operation 602, 604, 606 and/or 608.

Operation 602 illustrates detecting a heart rate of the first participant providing the communication content. For example, as shown in FIG. 1, the high-resolution camera of the communications content capture device 101 may externally image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel over a period of time indicating one or more heart beats. Such measurements over time may be used to compute a heart rate. The computed heart rate may be compared to a deceptive indicia threshold value maintained in the deceptive indicia threshold database 114. As an elevated heart rate may be an indicator of stress associated with providing deceptive communications content 102, a computed heart rate in excess of the deceptive indicia threshold value may be detected as indicia of deception in the communications content 102.

Operation 604 illustrates detecting a blood pressure of the first participant providing the communication content. For example, as shown in FIG. 1, the high-resolution camera of the communications content capture device 101 may externally image one or more blood vessels of the content-generating participant 103. The deceptive indicia detection module 113 may receive signals indicative of the blood vessel image and acquire measurements (e.g. pixel counts, reflectivity fluctuations, brightness, color, etc. in the blood vessel image) representing the various changes in size of the blood vessel. The size of the blood vessel at any given time may be used to compute a blood pressure. As an elevated blood pressure may be an indicator of stress associated with providing deceptive communications content 102, a computed blood pressure in excess of the deceptive indicia threshold value may be detected as indicia of deception in the communications content 102.

Operation 606 illustrates detecting a perspiration level of the first participant providing the communication content. For example, as shown in FIG. 1, the high-resolution camera of the communications content capture device 101 may image the skin surface of the content-generating participant 103. The deceptive indicia detection module 113 may receive signals associated with the image of the skin surface and detect the locations of one or more skin surface features, such as perspiration pores. The size of the perspiration pores and/or the dimensions of any perspiration droplets emanating from those pores may be measured (e.g. pixel counts, reflectivity fluctuations, brightness, color, etc in the skin surface image) and monitored for changes over time. As an elevated level of perspiration may be an indicator of stress associated with providing deceptive communications content 102, a computed perspiration level in excess of the deceptive indicia threshold value (e.g. a threshold pore or droplet dimension) may be detected as indicia of deception in the communications content 102.

Operation 608 illustrates detecting a breathing rate of the first participant providing the communication content. For example, as shown in FIG. 1, the communications content capture device 101 and/or the physiological data capture device 112 may include a high-resolution camera. The high-resolution camera may image the skin surface of the content-generating participant 103. The deceptive indicia detection module 113 may receive signals associated with the image of the content-generating participant 103 and detect the locations of one or more bodily features. The relative positions of such bodily features may be measured (e.g. pixel counts in the skin surface image) and monitored for changes over time. For example, movement of various bodily features (e.g. the expansion and contraction of the chest cavity, movement of the shoulders, etc.) may be indicative of respiration. As an elevated level of rate of respiration may be an indicator of stress associated with providing deceptive communications content 102, a computed breathing rate in excess of the deceptive indicia threshold value (e.g. a breathing rate) may be detected as indicia of deception in the communications content 102.

Figure 7:
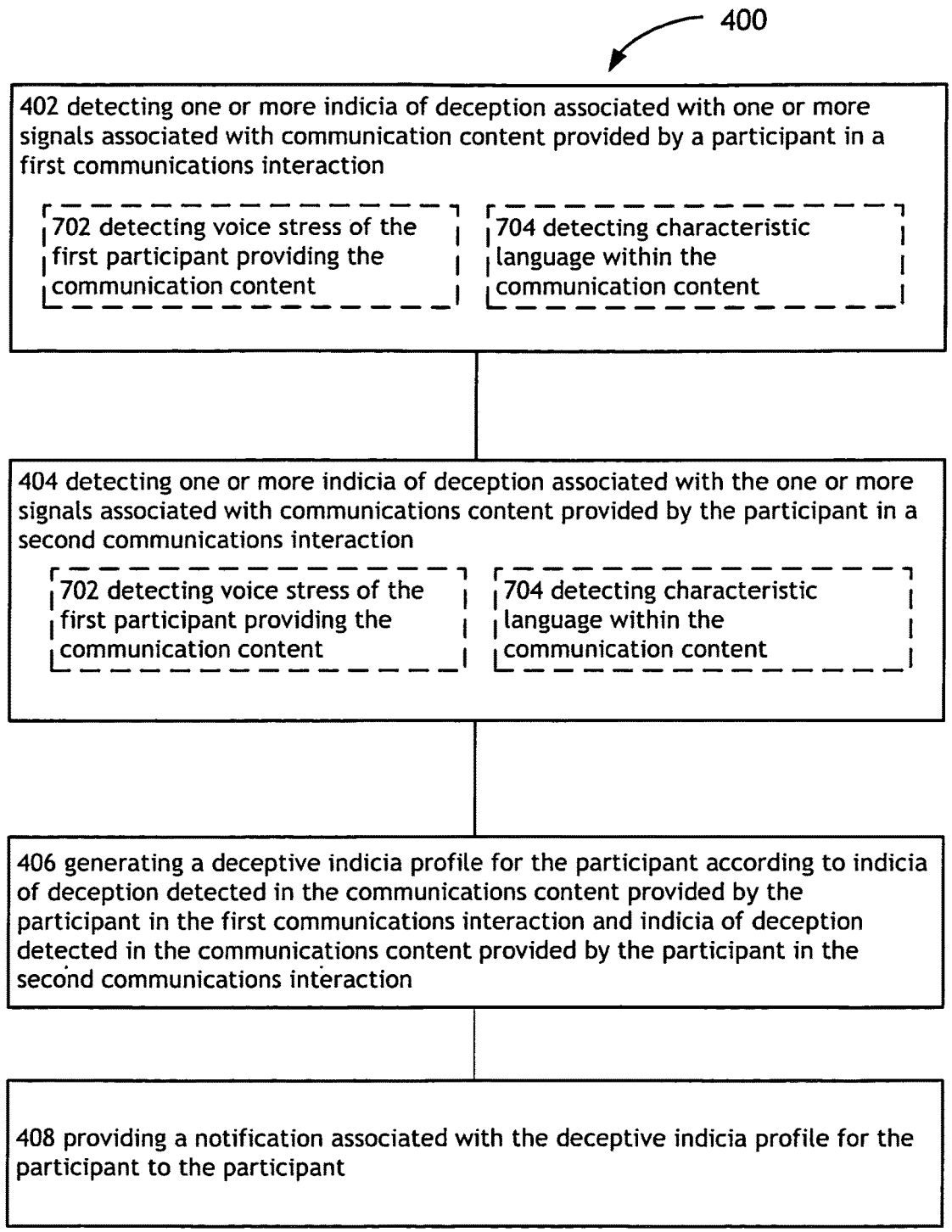
FIG. 7 shows an alternative embodiment of the operational procedure of FIG. 4.

FIG. 7 illustrates an example embodiment where the operations 402 and/or 404 of example operational flow 400 of FIG. 4 may include at least one additional operation. Additional operations may include an operation 702 and/or 704.

Operation 702 illustrates detecting voice stress of the first participant providing the communication content. For example, as shown in FIG. 1, the deceptive indicia detection module 113 may obtain a voice print of speech by the content-generating participant 103. Various types of voice-change may occur as a result of stress associated with providing deceptive communications content 102. For example, audible perceptible changes may include speaking rate, volume, voice tremor, spacing between syllables, and fundamental pitch or frequency of the voice. Further, inaudible changes may result from unconscious tensing of the vocal cords resulting in a dampening of selected frequency variations. When graphically portrayed, the difference may be readily discernible between unstressed or normal vocalization and vocalization under mild stress, attempts to deceive, or adverse attitudes. Still further, infrasonic, or subsonic, frequency modulation may be present, in some degree, in both the vocal cord sounds and in the formant sounds (e.g. between 8 and 12 Hz). The speech recognition engine of the deceptive indicia detection module 113 may detect the voice print representing communications content 102 and measure one or more audio characteristics (e.g. the audio frequency, pitch, volume, amplitude, etc., or stability thereof of portions of the voice print). An audio characteristic in excess of a deceptive indicia threshold value for the audio characteristic may be detected as indicia of deception in the communications content 102.

Operation 704 illustrates detecting characteristic language within the communication content. For example, the communications content capture device 101 may include a microphone. The microphone may capture speech content of the content-generating participant 103. The deceptive indicia detection module 113 may then analyze the audio signal and detect one or more characteristics of the audio signal. For example, the deceptive indicia detection module 113 may include a speech recognition engine for detecting the speech content of the content-generating participant 103 within the communications content 102. Various language constructs may be associated with the truth or falsity of speech content. For example, the use of formal or "distance" language may be indicative of deception in speech content. Examples of formal or "distance" language may include but are not limited to, usage of a multi-syllable versions of synonymous words (e.g. "exceptional" vs. "great"), avoidance of contractions (e.g. "cannot" instead of "can't"), impersonal pronoun usage (e.g. "one might think . . . " instead of "you might think . . . "), avoidance of commencing a sentence with a conjunction (e.g. "I thought . . . " instead of "But I thought . . . "), lack of antecedent basis for an article ("A man approached me and pointed a gun at me. He stuck the gun in my ribs and forced me into the car" where no prior reference to "a car" had been made), and the like. The speech recognition engine of the deceptive indicia detection module 113 may detect the speech terms used in the communications content 102 and measure one or more language usage parameters (e.g. the frequency of use of formal language, the proximity of one formal language instance to the next, etc.). A language usage parameter in excess of a deceptive indicia threshold value for the language usage parameter may be detected as indicia of deception in the communications content 102.

Figure 8:
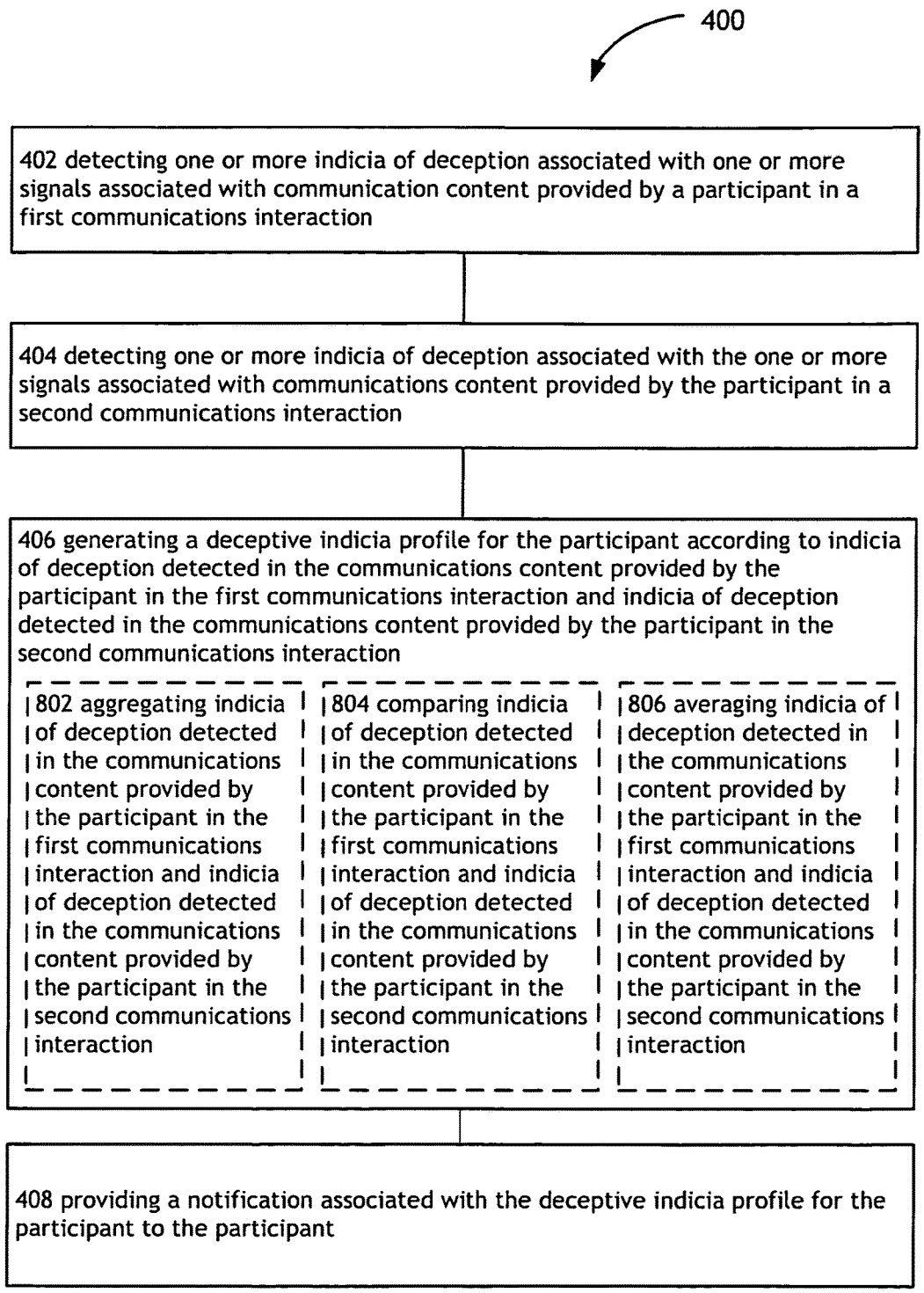
FIG. 8 shows an alternative embodiment of the operational procedure of FIG. 4.

FIG. 8 illustrates an example embodiment where the operations 406 of example operational flow 400 of FIG. 4 may include at least one additional operation. Additional operations may include an operation 802, 804 and/or 806.

Operation 802 illustrates aggregating indicia of deception detected in the communications content provided by the participant in the first communications interaction and indicia of deception detected in the communications content provided by the participant in the second communications interaction. For example, as shown in FIG. 1, the deceptive indicia detection module 113 may receive data associated with detected indicia of deception in communications content 102 provided by the content-generating participant 103 and/or retrieve data associated with detected indicia of deception in communications content 102 previously provided by the content-generating participant 103 and maintained in the deceptive indicia library database 129. The indicia of deception data may be aggregated (e.g. combined, summed, grouped, etc.) according to one or more parameters (e.g. indicia type, date of communication interaction, identity of the content-receiving participant 109, etc.) The aggregated indicia of deception data may be stored as a deceptive indicia profile 138 associated with the content-generating participant 103 and used to refine the deceptive indicia threshold associated with the content-generating participant 103 and maintained in the deceptive indicia threshold database 114.

Operation 804 illustrates comparing indicia of deception detected in the communications content provided by the participant in the first communications interaction and indicia of deception detected in the communications content provided by the participant in the second communications interaction. For example, as shown in FIG. 1, the deceptive indicia detection module 113 may receive data associated with detected indicia of deception in communications content 102 provided by the content-generating participant 103 and/or retrieve data associated with detected indicia of deception in communications content 102 previously provided by the content-generating participant 103 and maintained in the deceptive indicia library database 129. The indicia of deception data may be compared between the two or more communications. For example, indicia of deception associated with the movement of the eyes content-generating participant 103 may be detected in a first communications interaction as well as a second communications interaction. The movement of the eyes of the content-generating participant 103 in the first communications interaction may be compared to the move of the eyes of the content-generating participant 103 in the second communications interaction. The degree of correspondence between the two detected indicia of deception may be used to refine a participant profile characteristic (e.g. a threshold eye movement distance that constitutes an indicia of deception) for the content-generating participant 103. Specifically, if over a period of time the degree of departure from a normalized model that is characteristic of a particular indicia of deception changes, the normalized model and/or the threshold departure required for a detection of an indicia of deception may be modified according to the comparison of indicia of deception data between the two or more communications.

Operation 806 illustrates averaging indicia of deception detected in the communications content provided by the participant in the first communications interaction and indicia of deception detected in the communications content provided by the participant in the second communications interaction. For example, as shown in FIG. 1, the deceptive indicia detection module 113 may receive data associated with detected indicia of deception in communications content 102 provided by the content-generating participant 103 and/or retrieve data associated with detected indicia of deception in communications content 102 previously provided by the content-generating participant 103 and maintained in the deceptive indicia library database 129. The indicia of deception data may be averaged between the two or more communications interactions. For example, indicia of deception associated with the movement of the eyes content-generating participant 103 may be detected in a first communications interaction as well as a second communications interaction. The movement of the eyes of the content-generating participant 103 in the first communications interaction may be averaged with the movement of the eyes of the content-generating participant 103 in the second communications interaction. The average value associated with the respective indicia of deception data may be used to refine a participant profile characteristic (e.g. a threshold eye movement distance, frequency, direction, etc., that constitutes an indicia of deception) for the content-generating participant 103. Specifically, the participant profile characteristic may be set as the average of two or more indicia of deception from the two or more communications interactions.

Figure 9:
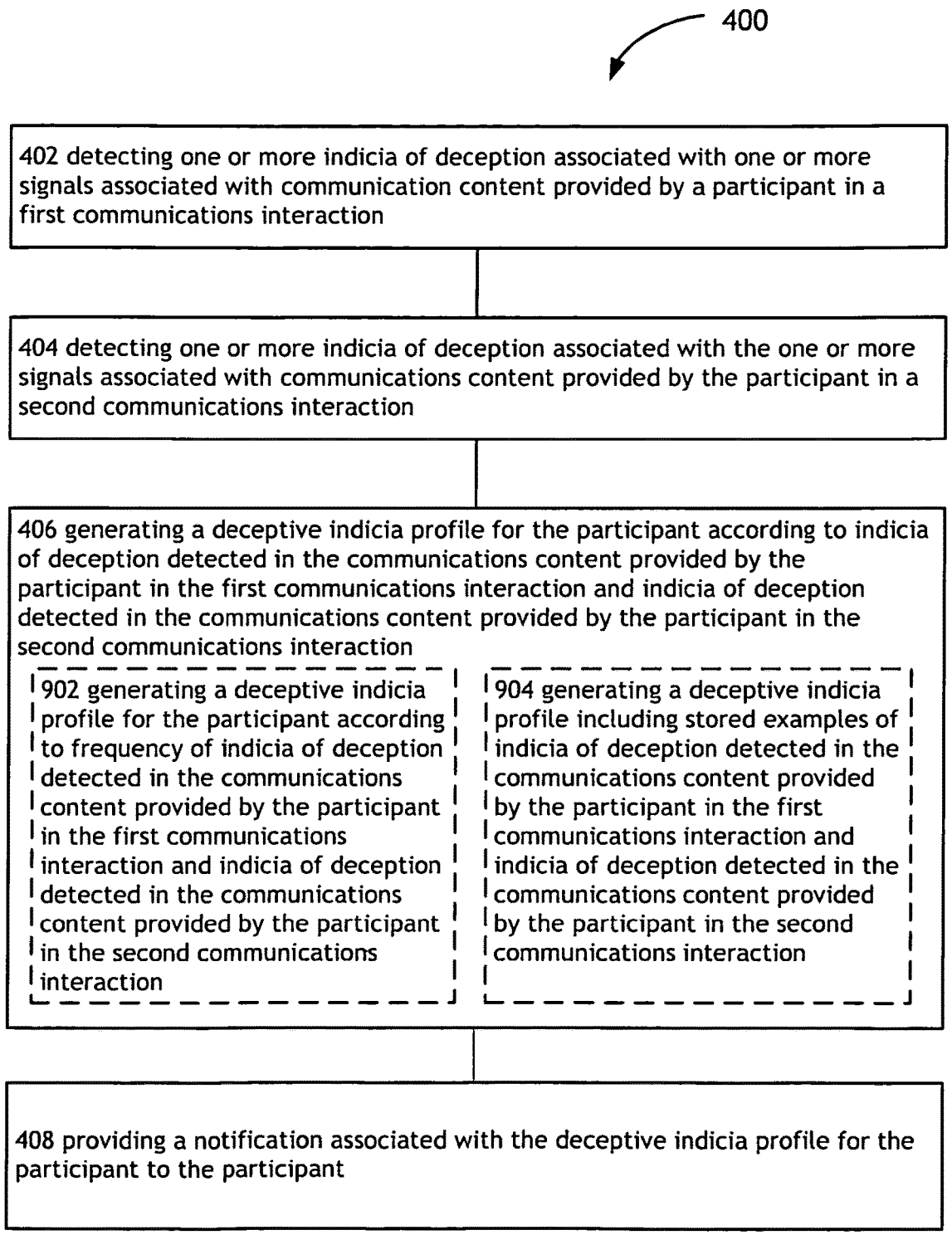
FIG. 9 shows an alternative embodiment of the operational procedure of FIG. 4.

FIG. 9 illustrates an example embodiment where the operations 406 of example operational flow 400 of FIG. 4 may include at least one additional operation. Additional operations may include an operation 902 and/or 904.

Operation 902 depicts generating a deceptive indicia profile for the participant according to frequency of indicia of deception detected in the communications content provided by the participant in the first communications interaction and indicia of deception detected in the communications content provided by the participant in the second communications interaction. For example, as shown in FIG. 1, the deceptive indicia detection module 113 may receive data associated with detected indicia of deception in communications content 102 provided by the content-generating participant 103 and/or retrieve data associated with detected indicia of deception in communications content 102 previously provided by the content-generating participant 103 and maintained in the deceptive indicia library database 129. The indicia of deception data may be analyzed to determine a frequency of a given indicia of deception within the communications content 102 provided by the content-generating participant 103 in the two or more communications interactions with the content-receiving participant 109A and/or the content-receiving participant 109B. For example, the frequency of the use of formal language may be detected in a first communications interaction as well as a second communications interaction. The frequencies may be may normalized for the length of each communications interaction and an overall frequency may be computed. This overall frequency may be stored to the deceptive indicia profile 138 associated with the content-generating participant 103 maintained by the deceptive indicia threshold database 114.

Operation 904 depicts generating a deceptive indicia profile including stored examples of indicia of deception detected in the communications content provided by the participant in the first communications interaction and indicia of deception detected in the communications content provided by the participant in the second communications interaction. For example, as shown in FIG. 1, the deceptive indicia detection module 113 may receive data associated with detected indicia of deception in communications content 102 provided by the content-generating participant 103 and/or retrieve data associated with detected indicia of deception in communications content 102 previously provided by the content-generating participant 103 and maintained in the deceptive indicia library database 129. The indicia of deception data may be analyzed to determine an exemplary instance of a given indicia of deception within the communications content 102 provided by the content-generating participant 103 in the two or more communications interactions with the content-receiving participant 109A and/or the content-receiving participant 109B. For example, video footage associated with a common micro expression presented in each of the two or more communications interactions may be stored to the deceptive indicia profile 138 associated with the content-generating participant 103 maintained by the deceptive indicia threshold database 114.

Figure 10:
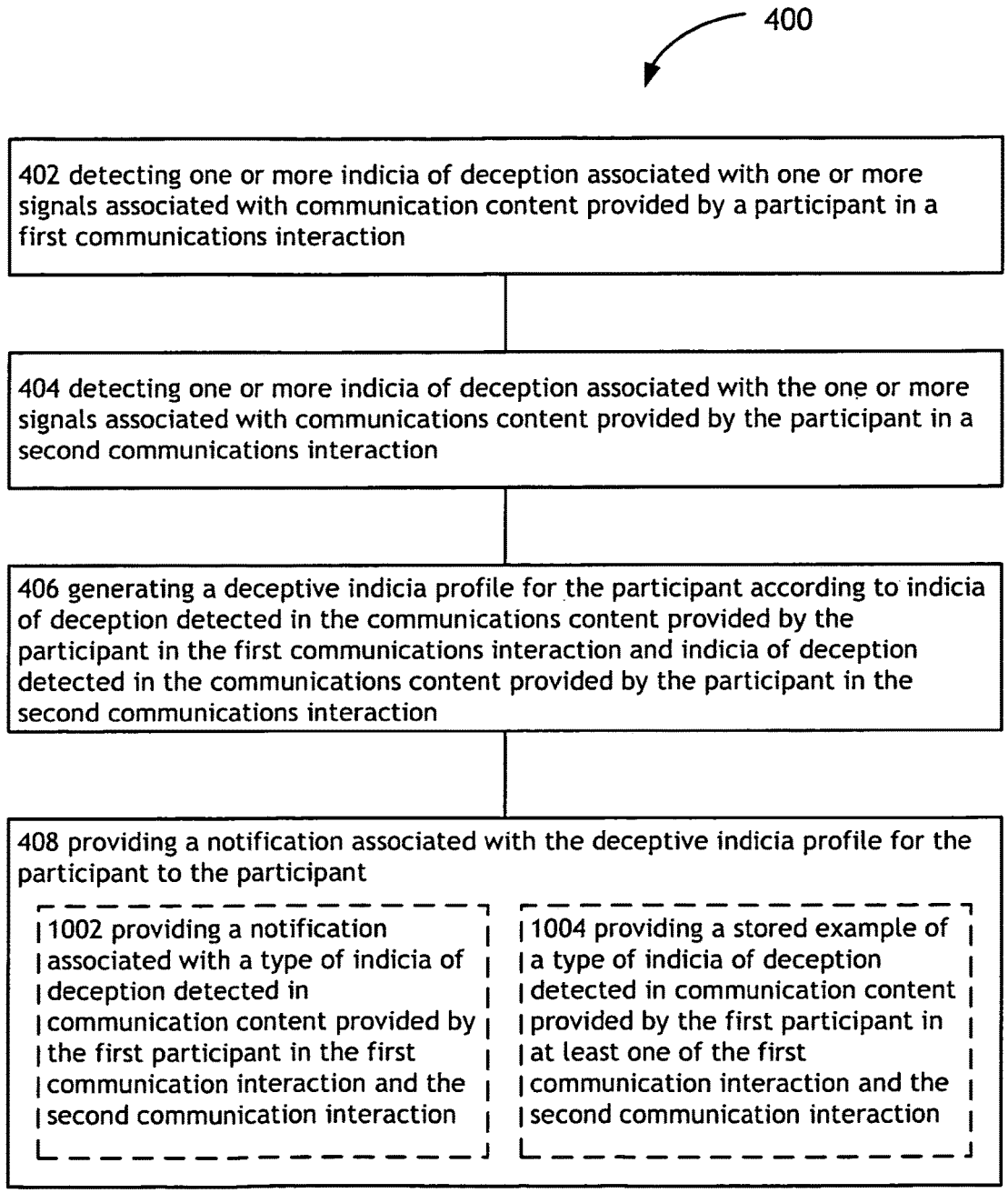
FIG. 10 shows an alternative embodiment of the operational procedure of FIG. 4.

FIG. 10 illustrates an example embodiment where the operation 408 of example operational flow 400 of FIG. 4 may include at least one additional operation. Additional operations may include an operation 1002 and/or 1004.

Figure 2B:
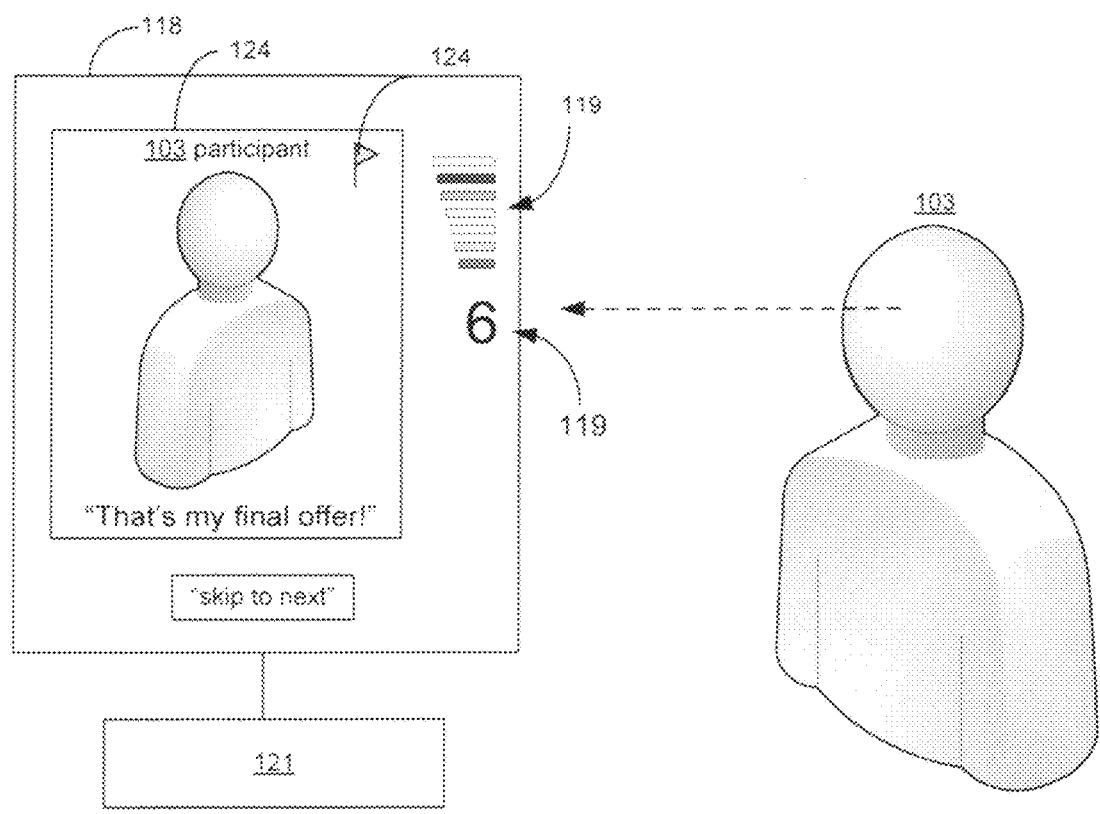
FIG. 2B shows an exemplary high-level block diagram of an exemplary system.

Operation 1002 depicts providing a notification associated with a type of indicia of deception detected in communication content provided by the first participant in the first communication interaction and the second communication interaction. For example, as shown in FIGS. 1 and 2A-2B, a content-generating participant 103 may provide one or more inputs to user input device 121 to make a selection of one or more types of indicia of deception of interest associated with the content-generating participant 103. The deceptive indicia notification module 116 may retrieve stored indicia of deception data maintained in the deceptive indicia profile 138 associated with the content-generating participant 103 for display on the deceptive indicia display device 118. For example, a content-receiving participant 109 may desire to view detection metrics (e.g. frequency, duration, degree of departure from a normalized model, etc.) associated with of a selected type of indicia of deception (e.g. micro expressions) detected in two or more communications interactions with a content-receiving participant 109. The deceptive indicia notification module 116 may retrieve data associated with one or more instances of the selected type of indicia of deception (e.g. the frequency of micro expressions in the two or more communications interactions) and display data for the content-receiving participant 109 on the deceptive indicia display device 118.

Operation 1004 depicts providing a stored example of a type of indicia of deception detected in communication content provided by the first participant in at least one of the first communication interaction and the second communication interaction. For example as shown in FIGS. 1 and 2A-2B, a content-generating participant 103 may provide one or more inputs to user input device 121 to make a selection of one or more types of indicia of deception of interest associated with the content-generating participant 103. The deceptive indicia notification module 116 may retrieve stored examples of the indicia of deception maintained in the deceptive indicia profile 138 associated with the content-generating participant 103 for display on the deceptive indicia display device 118. For example, a content-receiving participant 109 may desire to view one or more instances of a selected type of indicia of deception (e.g. pupil dilation) detected in two or more communications interactions with the content-receiving participant 109. The deceptive indicia notification module 116 may retrieve data associated with one or more instances of the selected type of indicia of deception (e.g. video footage of the micro expressions) and display data for the content-receiving participant 109 on the deceptive indicia display device 118.

Figure 11:
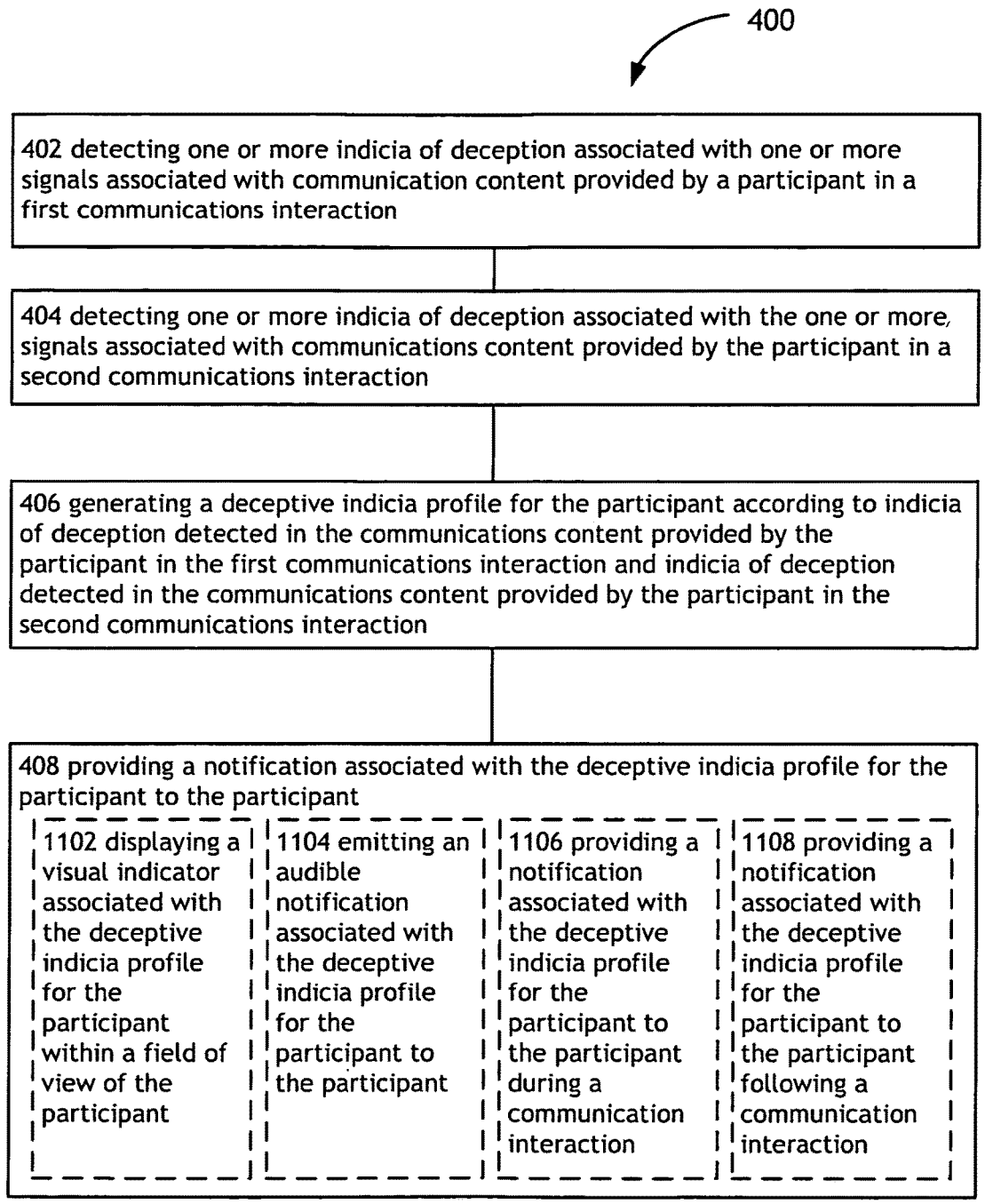
FIG. 11 shows an alternative embodiment of the operational procedure of FIG. 4.

FIG. 11 illustrates an example embodiment where the operation 408 of example operational flow 400 of FIG. 4 may include at least one additional operation. Additional operations may include an operation 1102, 1104, 1106 and/or 1108.

Operation 1102 depicts displaying a visual indicator associated with the deceptive indicia profile for the participant within a field of view of the participant. For example, as shown in FIGS. 1 and 2A-2B, upon the receipt of one or more signals associated with the presence of indicia of deception in communications content 102 from the deceptive indicia detection module 113 as determined according to a comparison with the deceptive indicia profile 138, the deceptive indicia notification module 116 may provide one or more video signals to a deceptive indicia display device 118 (e.g. an LCD display) so that a visual indicator 130 associated with the indicia of deception is presented within a field of view of the content-receiving participant 109. As shown in FIG. 2A, the deceptive indicia display device 118 may display a video conferencing interface 120 configured to present audio/video content from the content-generating participant 103 during a communication interaction (e.g. at least one of audio and visual communication between at least the content-generating participant 103 and content-receiving participant 109). The deceptive indicia display device 118 may further display the visual indicator 130 (e.g. a color coded indicator) that presents a cumulative number of occurrences of indicia of deception in the communications content 102, a rate of occurrences of indicia of deception in the communications content 102, and the like. The visual indicator 130 may be a dynamic indicator that changes (e.g. moves from an indicated "high" rate of indicia of deception to an indicated "low" rate of indicia of deception) in real-time according to the type and/or amount of indicia of deception detected within communications content 102.

Operation 1104 illustrates emitting an audible notification associated with the deceptive indicia profile for the participant to the participant. For example, as shown in FIG. 1, upon the receipt of one or more signals associated with the presence of indicia of deception in communications content 102 from the deceptive indicia detection module 113 as determined according to a comparison with the deceptive indicia profile 138, the deceptive indicia notification module 116 may provide one or more audio signals to an audio speaker 111 (e.g. an audio speaker, headset, earpiece, etc.) that an audio indicator (e.g. a notification sound effect such as a beep, a spoken message, etc.) associated with the indicia of deception is emitted to the content-receiving participant 109.

Operation 1106 illustrates providing a notification associated with the deceptive indicia profile for the participant to the participant during a communication interaction. For example, as shown in FIGS. 1 and 2A, it may be the case that the deceptive indicia detection module 113 and deceptive indicia notification module 116 may perform deceptive indicia detection and notification (as described above) in a substantially real-time manner during a communication interaction (e.g. a video conference) between the content-generating participant 103 and the content-receiving participant 109 to allow the content-receiving participant 109 to monitor the communications content 102 for indicia of deception and account for such indicia of deception in their consideration of the veracity of the communications content 102 received from the content-generating participant 103.

Operation 1108 illustrates providing a notification associated with the deceptive indicia profile for the participant to the participant following a communication interaction. For example, as shown in FIGS. 1 and 2B, upon completion of a communications interaction, it may be advisable for a content-receiving participant 109 to review the communications content 102 and any detected indicia of deception for education and/or training purposes. During a communication interaction, the deceptive indicia detection module 113 may detect an incidence of indicia of deception. The deceptive indicia detection module 113 may store a record associated with the detected indicia of deception to a deceptive indicia library database 129. Following the communications interaction, one or more portions of the communications content 102 may be retrieved from the deceptive indicia library database 129 and displayed/broadcasted by the presentation module 117 via a review interface 133. The review interface 133 may include video playback functionality configured to present the communications content 102 according to the records associated with the detected indicia of deception. The review interface 133 may allow for the content-generating participant 103 to skip to portions of the communications content 102 associated with the records associated with the detected indicia of deception. For example, the review interface 133 may provide a "skip to next" user interface element whereby a user input associated with the "skip to next" user interface element causes the review interface 133 to display/broadcast the next instance of the communications content 102 having a record associated with a detection of indicia of deception.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim 1ncludes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed is:

1. A system comprising:
   means for detecting one or more indicia of deception associated with one or more signals associated with communication content provided by a participant in a first communications interaction;
   means for detecting one or more indicia of deception associated with one or more signals associated with communications content provided by the participant in a second communications interaction;
   means for generating a deceptive indicia profile for the participant according to indicia of deception detected in the communications content provided by the participant in the first communications interaction and indicia of deception detected in the communications content provided by the participant in the second communications interaction; and
   means for providing a notification associated with the deceptive indicia profile for the participant to the participant.

2. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting one or more micro expressions of the first participant providing the communication content.

3. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting an eye dilation of the first participant providing the communication content.

4. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting an eye movement of the first participant providing the communication content.

5. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting a heart rate of the first participant providing the communication content.

6. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting a blood pressure of the first participant providing the communication content.

7. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting a perspiration level of the first participant providing the communication content.

8. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting a breathing rate of the first participant providing the communication content.

9. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
   means for detecting voice stress of the first participant providing the communication content.

10. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
    means for detecting characteristic language within the communication content.

11. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
    means for aggregating indicia of deception detected in the communications content provided by the participant in the first communications interaction and indicia of deception detected in the communications content provided by the participant in the second communications interaction.

12. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
    means for comparing indicia of deception detected in the communications content provided by the participant in the first communications interaction and indicia of deception detected in the communications content provided by the participant in the second communications interaction.

13. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
    means for averaging indicia of deception detected in the communications content provided by the participant in the first communications interaction and indicia of deception detected in the communications content provided by the participant in the second communications interaction.

14. The system of claim 1, wherein at least one of the means for detecting one or more indicia of deception associated with one or more signals associated with communication content provided by a participant in a first communications interaction or the means for detecting one or more indicia of deception associated with one or more signals associated with communications content provided by the participant in a second communications interaction comprise:
    means for generating a deceptive indicia profile for the participant according to frequency of indicia of deception detected in the communications content provided by the participant in the first communications interaction and indicia of deception detected in the communications content provided by the participant in the second communications interaction.

15. The system of claim 1, wherein the means for generating a deceptive indicia profile for the participant according to indicia of deception detected in the communications content provided by the participant in the first communications interaction and indicia of deception detected in the communications content provided by the participant in the second communications interaction comprises:
    means for generating a deceptive indicia profile including stored indicia of deception detected in the communications content provided by the participant in the first communications interaction and indicia of deception detected in the communications content provided by the participant in the second communications interaction.

16. The system of claim 1, wherein the means for providing a notification associated with the deceptive indicia profile for the participant to the participant comprises:
    means for providing a notification associated with a frequency of indicia of deception detected in communication content provided by the first participant in the first communication interaction and the second communication interaction.

17. The system of claim 1, wherein the means for providing a notification associated with the deceptive indicia profile for the participant to the participant comprises:
    means for providing a notification associated with a type of indicia of deception detected in communication content provided by the first participant in the first communication interaction and the second communication interaction.

18. The system of claim 1, wherein the means for providing a notification associated with the deceptive indicia profile for the participant to the participant comprises:
    means for providing a stored indicia of deception detected in communication content provided by the first participant in at least one of the first communication interaction or the second communication interaction.

19. The system of claim 1, wherein the means for providing a notification associated with the deceptive indicia profile for the participant to the participant comprises:
    means for displaying a visual indicator associated with the deceptive indicia profile for the participant within a field of view of the participant.

20. The system of claim 1, wherein the means for providing a notification associated with the deceptive indicia profile for the participant to the participant comprises:
    means for emitting an audible notification associated with the deceptive indicia profile for the participant to the participant.

21. The system of claim 1, wherein the means for providing a notification associated with the deceptive indicia profile for the participant to the participant comprises:
    means for providing a notification associated with the deceptive indicia profile for the participant to the participant during a communication interaction.

22. The system of claim 1, wherein the means for providing a notification associated with the deceptive indicia profile for the participant to the participant comprises:
    means for providing a notification associated with the deceptive indicia profile for the participant to the participant following a communication interaction.

23. A method comprising:
    detecting one or more indicia of deception associated with one or more signals associated with communication content provided by a participant in a first communications interaction;

detecting one or more indicia of deception associated with one or more signals associated with communications content provided by the participant in a second communications interaction;

generating a deceptive indicia profile for the participant according to indicia of deception detected in the communications content provided by the participant in the first communications interaction and indicia of deception detected in the communications content provided by the participant in the second communications interaction; and providing a notification associated with the deceptive indicia profile for the participant to the participant.

24. A non-transitory computer-readable medium comprising computer-readable instructions for executing a computer implemented method, the method comprising:

detecting one or more indicia of deception associated with one or more signals associated with communication content provided by a participant in a first communications interaction;

detecting one or more indicia of deception associated with one or more signals associated with communications content provided by the participant in a second communications interaction;

generating a deceptive indicia profile for the participant according to indicia of deception detected in the communications content provided by the participant in the first communications interaction and indicia of deception detected in the communications content provided by the participant in the second communications interaction; and providing a notification associated with the deceptive indicia profile for the participant to the participant.

* * * * *